United States Patent [19]

Hosoi et al.

[11] Patent Number: 5,610,671
[45] Date of Patent: Mar. 11, 1997

[54] OPHTHALMIC APPARATUS

[75] Inventors: Yoshinobu Hosoi, Gamagori; Hirohisa Terabe, Toyokawa, both of Japan

[73] Assignee: Nidek Co., Ltd., Japan

[21] Appl. No.: 591,798

[22] Filed: Jan. 25, 1996

[30] Foreign Application Priority Data

Jan. 31, 1995 [JP] Japan .................................. 7-036094

[51] Int. Cl.⁶ .............................. A61B 3/00; A61B 3/10; A61B 3/02; G05B 19/02
[52] U.S. Cl. ......................... 351/200; 351/205; 351/222; 364/580
[58] Field of Search .................................... 351/200, 201, 351/204, 205, 222, 246, 223, 211, 229; 364/579, 580

[56] References Cited

U.S. PATENT DOCUMENTS 5,444,504  8/1995  Kobayashi et al. ....................... 351/237
5,490,098  2/1996  Kardon ................. 351/200 X

FOREIGN PATENT DOCUMENTS 6-254050  9/1994  Japan .
6-339462  12/1994  Japan .

Primary Examiner—Huy Mai
Attorney, Agent, or Firm—Finnegan, Henderson, Farabow, Garrett & Dunner

[57] ABSTRACT

Disclosed herein is an ophthalmic apparatus for obtaining a refractive corrected-degree based on a refractive power of each of eyes to be examined, the ophthalmic apparatus comprising a refractive power inspecting device for inspecting the refractive power of the each eye, a program storing device for storing therein a program for measuring completely-corrected degrees of the eyes, adjusting the completely-corrected degrees according to factors for adjusting degrees to be corrected and thereby predicting degrees to be prescribed, an input device for inputting data about the factors for adjusting the degrees to be corrected, a program conducting device for advancing the program stored in the program storing device, a control device for sequentially activating the ophthalmic apparatus in accordance with the program and processing the result of inspection by completely-corrected degree inspecting device and the data input by the input device thereby to predict prescribed degrees, and a display device for displaying the prescribed degrees predicted by the control device. Thus, an examiner having little experience in and unfamiliar to the optometry can easily obtain suitable prescribed values.

15 Claims, 48 Drawing Sheets

FIG. 4

| ITEM | CONTENTS | | | | | | |
|---|---|---|---|---|---|---|---|
| OBJECT | VISION REDUCTION | FOR LICENSE | REGULAR INSPECTION | SPARE | GLASS CHANGE | FRAME CHANGE | OTHERS |
| AGE | ~15 | ~25 | ~35 | ~45 | ~55 | ~65 | ~75 | 76~ |
| SEX | MALE | FEMALE | | | | | |
| OCCUPATION | STUDENT | COMPANY EMPLOYEE | INDEPENDENT ENTERPRISE | DRIVER | OTHERS | | |
| HOBBY | SPORT | READING | OTHERS | | | | |
| HISTORY OF SPECTACLES | NO | YES | DAILY USE | FOR NEAR SIGHT | PROGRESSION | | |
| HISTORY OF CL | NO | YES | H | S | | | |

CASE HISTORY

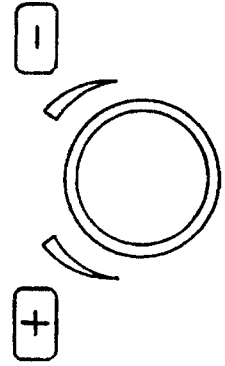

⇐ ⇒  SELECT ITEMS BY ↑ AND ↓

SELECT CONTENTS BY KNOB OR + − SWITCH

\* Priority is given to eye good in previous spectacle vision

FIG. 6 (b)

| | |
|---|---|
| S0 ... | Monocular complete correction |
| S1 ... | Vision for R and L $\geqq$ 0.7 ? |
| S2 ... | Require close inspection |
| S3 ... | Vision balance ? |
| S4 ... | Add S + 0.25 to L eye |
| S5 ... | Vision balance ? |
| S6 ... | Previous spectacles * dominant eye ? |
| S7 ... | Add S − 0.25 to L eye |
| S8 ... | Add S + 0.25 to R eye |
| S9 ... | Vision balance? |
| S10 ... | Previous spectacles * dominant eye ? |
| S11 ... | Add S − 0.25 to R eye |
| S12 ... | Binocular complete correction |
| S13 ... | Adjust corrected degrees |

FIG. 8 (a)

Table A  <Adjust degree of myopia
[upon initial spectacles wear]>

| Complete correction S1 | Degree to be reduced ΔS1 | Degree to be adjusted S1´ S1−ΔS1 |
|---|---|---|
| −0.25 | } −0.25 | 0 |
| −0.50 |  | −0.25 |
| −0.75 |  | −0.50 |
| −1.00 |  | −0.75 |
| −1.25 | } −0.50 | −0.75 |
| −1.50 |  | −1.00 |
| −1.75 |  | −1.25 |
| −2.00 | } −0.75 | −1.25 |
| −2.25 |  | −1.50 |
| −2.50 | } −1.00 | −1.50 |
| −2.75 |  | −1.75 |
| −3.00 | } −1.25 | −1.75 |
| −3.25 |  | −2.00 |
| −3.50 | } −1.50 | −2.00 |
| −3.75 |  | −2.25 |
| −4.00 | } −1.75 | −2.25 |
| −4.25 |  | −2.50 |
| −4.50 | −2.00 | −2.50 |
| −4.75 | −2.25 | −2.50 |
| −5.00 | −2.50 | −2.50 |
| . | . | . |
| . | . | . |

FIG. 8 (a)

Table A  <Adjust degree of myopia
          [upon initial spectacles wear]>

| Complete correction S1 | Degree to be reduced ΔS1 | Degree to be adjusted S1´ S1−ΔS1 |
|---|---|---|
| −0.25 | ⎫ | 0 |
| −0.50 | ⎬ −0.25 | −0.25 |
| −0.75 | ⎪ | −0.50 |
| −1.00 | ⎭ | −0.75 |
| −1.25 | ⎫ | −0.75 |
| −1.50 | ⎬ −0.50 | −1.00 |
| −1.75 | ⎭ | −1.25 |
| −2.00 | ⎫ | −1.25 |
| −2.25 | ⎬ −0.75 | −1.50 |
| −2.50 | ⎭ | −1.50 |
| −2.75 | ⎫ −1.00 | −1.75 |
| −3.00 | ⎭ | −1.75 |
| −3.25 | ⎫ −1.25 | −2.00 |
| −3.50 | ⎭ | −2.00 |
| −3.75 | ⎫ −1.50 | −2.25 |
| −4.00 | ⎭ | −2.25 |
| −4.25 | ⎫ −1.75 | −2.50 |
| −4.50 | ⎭ | −2.50 |
| −4.75 | −2.00 | −2.50 |
| −5.00 | −2.25 | −2.50 |
|  | −2.50 |  |
| . | . | . |
| . | . | . |

FIG. 8 (b)

Table B  <Adjust degree of myopia
         [upon second spectacles wear]>

| Difference between degree of old spectacles and completely corrected degree $S_2$ | Degree to be reduced $\Delta S_2$ | Degree to be adjusted $S_2{-}\Delta S_2$ |
|---|---|---|
| -0.25 | 0 | -0.25 |
| -0.50 |  | -0.25 |
| -0.75 | } -0.25 | -0.50 |
| -1.00 |  | -0.50 |
| -1.25 | } -0.50 | -0.75 |
| -1.50 |  | -1.00 |
| -1.75 |  | -1.00 |
| -2.00 | } -0.75 | -1.25 |
| -2.25 | -1.00 | -1.25 |
| -2.50 |  | -1.25 |
| -2.75 | } -1.25 | -1.50 |
| -3.00 | -1.50 | -1.50 |
| ⋮ | ⋮ | ⋮ |

Better to increase
the degree up to -0.75
(-1.00 at strong level)

FIG. 9 (a)

Table C <Adjust degree of astigmatism
[upon initial spectacles wear]>

| Complete correction $C1$ | Degree to be reduced $\Delta C1$ | Degree to be adjusted $C1'$ $C1-\Delta C1$ |
|---|---|---|
| -0.25 |  } -0.25 | 0 |
| -0.50 |  | -0.25 |
| -0.75 |  | -0.50 |
| -1.00 |  } -0.50 | -0.50 |
| -1.25 |  | -0.75 |
| -1.50 |  } -0.75 | -0.75 |
| -1.75 |  | -1.00 |
| -2.00 |  } -1.00 | -1.00 |
| -2.25 |  | -1.25 |
| -2.50 |  | -1.50 |
| -2.75 |  } -1.25 | -1.50 |
| -3.00 |  | -1.75 |
| -3.25 |  } -1.50 | -1.75 |
| -3.50 |  | -2.00 |
| -3.75 |  | -2.00 |
| ⋮ | ⋮ | ⋮ |

FIG. 9 (b)

Table D <Adjust degree of astigmatism
[upon second spectacles wear]>

| Difference between degree of old spectacles and completely corrected degree $C2$ | Degree to be reduced $\Delta C2$ | Degree to be adjusted $C2'$ $C2-\Delta C2$ |
|---|---|---|
| -0.25 | 0 | -0.25 |
| -0.50 |  | -0.25 |
| -0.75 | } -0.25 | -0.50 |
| -1.00 |  | -0.75 |
| -1.25 | -0.50 | -0.75 |
| -1.50 |  |  |
| -1.75 |  |  |
| -2.00 | } $C2+0.75$ |  |
| -2.25 |  |  |
| -2.50 |  |  |
| -2.75 |  |  |
| -3.00 |  |  |
| -3.25 |  |  |
| ⋮ | ↓ | ↓ |

FIG. 10 (b)

| | |
|---|---|
| 1-1 ··· | Anisometropia ?<br>Difference in S or C between R and L > 1 |
| 1-2 ··· | Astigmatism ? |
| 1-3 ··· | Astigmatism ? |
| 1-4 ··· | Oblique astigmatism ? |
| 1-5 ··· | Oblique astigmatism ? |
| 1-6 ··· | S value ? |
| 1-7 ··· | S value ? |
| 1-8 ··· | S value ? |
| 1-9 ··· | S value ? |
| 1-10 ··· | S value ? |
| 1-11 ··· | S value ? |

FIG. 11 (b)

| | |
|---|---|
| 2-1 ··· | Main appeal |
| 2-2 ··· | Easy to see ? |
| 2-3 ··· | S > 0 |
| 2-4 ··· | Add S − 0.25 to both eyes |
| 3-1 ··· | Initial spectacles wear ? |
| 3-2 ··· | Effect Δ S1 subtraction process on both eyes based on table A with degree-strong eye as reference |
| 3-3 ··· | Effect Δ S2 subtraction process on both eyes based on table B with degree-strong eye as reference |
| 3-4 ··· | Easy to see ? |
| 3-5 ··· | S < binocular completely corrected degree S ? |
| 3-6 ··· | Add S − 0.25 to both eyes |

(Binocular vision confirmation step)

FIG. 12 (b)

| | |
|---|---|
| 4-1 ··· | Initial spectacles wear ? |
| 4-2 ··· | Effect $\Delta C1$ subtraction process on both eyes based on table C with degree-strong eye as reference |
| 4-3 ··· | Add $\Delta C1/2$ to binocular equivalent spherical surface S |
| 4-4 ··· | Effect $\Delta C2$ subtraction process on both eyes based on table D with degree-strong eye as reference |
| 4-5 ··· | Add $\Delta C2/2$ to binocular equivalent spherical surface S |
| 5-1 ··· | Initial spectacles wear ? |
| 5-2 ··· | Effect $\Delta C1$ subtraction process on both eyes based on table C with degree-strong eye as reference |
| 5-3 ··· | Effect $\Delta S1$ subtraction process on both eyes based on table A with degree-strong eye as reference |
| 5-4 ··· | Effect $\Delta C2$ subtraction process on both eyes based on table D with degree-strong eye as reference |
| 5-5 ··· | Effect $\Delta S2$ subtraction process on both eyes based on table B with degree-strong eye as reference |
| 5-6 ··· | Physical disorder ? |
| 5-7 ··· | Add C + 0.25 to both eyes or add S + 0.25 to both eyes |
| 5-8 ··· | Easy to see ? |
| 5-9 ··· | S < binocular completely corrected degree S ? |
| 5-10 ··· | Add S − 0.25 to both eyes |

FIG. 13 (b)

| | |
|---|---|
| 6-1 ··· | Initial spectacles wear ? |
| 6-2 ··· | C ≦ − 0.5 |
| 6-3 ··· | C ≦ − 0.5 |
| 6-4 ··· | Effect Δ C1 subtraction process on both eyes based on table C with degree-strong eye as reference |
| 6-5 ··· | Add Δ C1/2 to binocular equivalent spherical surface S |
| 6-6 ··· | Add C/2 to equivalent spherical surface S |
| 6-7 ··· | Effect Δ C2 subtraction process on both eyes based on table D with degree-strong eye as reference |
| 6-8 ··· | Add Δ C2/2 to binocular equivalent spherical surface S |
| 6-9 ··· | Astigmatism exists in previous spectacles C ? |
| 6-10 ··· | Physical disorder ? |
| 6-11 ··· | Add C + 0.25 to both eyes or vary AXIS |

(Binocular vision confirmation step)

FIG. 14 (b)

| | |
|---|---|
| 7-1 ··· | Initial spectacles wear ? |
| 7-2 ··· | C ≦ − 0.5 |
| 7-3 ··· | C ≦ − 0.5 |
| 7-4 ··· | Hold spherical surface as it is |
| 7-5 ··· | Effect Δ S1 subtraction process on both eyes based on table A with degree-strong eye as reference |
| 7-6 ··· | Effect Δ C1 subtraction process on both eyes based on table C with degree-strong eye as reference |
| 7-7 ··· | Effect Δ S1 subtraction process on both eyes based on table A with degree-strong eye as reference |
| 7-8 ··· | Physical disorder ? |
| 7-9 ··· | Add C + 0.25 to both eyes or vary AXIS |
| 7-10 ··· | Easy to see ? |
| 7-11 ··· | S < binocular completely corrected degree S ? |
| 7-12 ··· | Add S − 0.25 to both eyes |
| 7-13 ··· | Effect Δ C2 subtraction process on both eyes based on table D with degree-strong eye as reference |
| 7-14 ··· | Effect Δ S2 subtraction process on both eyes based on table B with degree-strong eye as reference |
| 7-15 ··· | Astigmatism exists in previous spectacles ? |
| 7-16 ··· | Hold spherical surface as it is |
| 7-17 ··· | Effect Δ S2 subtraction process on both eye based on table B with degree-strong eye as reference |

(Binocular vision confirmation step)

FIG. 15 (b)

| | |
|---|---|
| 8-1 ··· | Initial spectacles wear ? |
| 8-2 ··· | Set degree-strong eye and degree-weak eye to the same degree |
| 8-3 ··· | Add S + 0.75 to degree-strong eye |
| 8-4 ··· | Add S + 0.75 to previous degree of degree-strong eye or completely correct degree-strong eye |
| 8-5 ··· | Main appeal |
| 8-6 ··· | Easy to see ? |
| 8-7 ··· | S > 0 |
| 8-8 ··· | Add S - 0.25 to both eyes |
| 8-9 ··· | Physical disorder ? |
| 8-10 ··· | Strong S = weak S ? |
| 8-11 ··· | Add S - 0.25 to degree-strong eye |

FIG. 16 (b)

| | | |
|---|---|---|
| 9-1 | ··· | Initial spectacles wear ? |
| 9-2 | ··· | Set both eyes to S1' based on table A with degree-weak eye as reference |
| 9-3 | ··· | Add S - 0.75 to degree-strong eye |
| 9-4 | ··· | Set degree-weak eye to degree reduced by Δ2 based on table B |
| 9-5 | ··· | Add S - 0.75 to previous degree of degree-strong eye or completely correct degree-strong eye |
| 9-6 | ··· | Easy to see ? |
| 9-7 | ··· | S < binocular completely corrected degree S ? |
| 9-8 | ··· | Add S - 0.25 to both eyes |

FIG. 17 (b)

| | |
|---|---|
| 10-1 ··· | Type of anisometropia |
| 10-2 ··· | Initial spectacles wear ? |
| 10-3 ··· | Initial spectacles wear ? |
| 10-4 ··· | Initial spectacles wear ? |
| 10-5 ··· | Effect $\Delta C1$ subtraction process on both eyes based on table C with degree-strong eye as reference |
| 10-6 ··· | Add $\Delta C1/2$ to binocular equivalent spherical surface S |
| 10-7 ··· | Add S + 0.75 to degree-strong eye |
| 10-8 ··· | Effect $\Delta C2$ subtraction process on both eyes based on table D with degree-strong eye as reference |
| 10-9 ··· | Add $\Delta C2/2$ to binocular equivalent spherical surface S |
| 10-10 ··· | Add S + 0.75 to previous degree of degree-strong eye or completely correct degree-strong eye |
| 10-11 ··· | Set both eyes to C1' based on table C with degree-weak eye as reference |
| 10-12 ··· | Add $\Delta C1/2$ to binocular equivalent spherical surface S |
| 10-13 ··· | Add C - 0.75 to degree-strong eye |

FIG. 17 (c)

| | |
|---|---|
| 10-14 ··· | Set degree-weak eye to degree reduced by $\Delta C2$ based on table D |
| 10-15 ··· | Add $\Delta C2/2$ to binocular equivalent spherical surface S |
| 10-16 ··· | Add C - 0.75 to previous degree of degree-strong eye or completely correct degree-strong eye |
| 10-17 ··· | Set both eyes to C1' based on table C with degree-weak eye as reference |
| 10-18 ··· | Add $\Delta C1/2$ to binocular equivalent spherical surface S |
| 10-19 ··· | Add C - 0.75 to degree-strong eye |
| 10-20 ··· | Add S + 0.75 to degree-strong eye |
| 10-21 ··· | Set degree-weak eye to degree reduced by $\Delta C2$ based on table D |
| 10-22 ··· | add $\Delta C2/2$ to binocular equivalent spherical surface S |
| 10-23 ··· | Add C - 0.75 to previous degree of degree-strong eye or completely correct degree-strong eye |
| 10-24 ··· | Add S + 0.75 to previous degree of degree-strong eye or completely correct degree-strong eye |

FIG. 18 (b)

| | |
|---|---|
| 10-25 ··· | Main appeal |
| 10-26 ··· | Easy to see ? |
| 10-27 ··· | S > 0 |
| 10-28 ··· | Add S − 0.25 to both eyes |
| 11-25 ··· | Physical disorder ? |
| 11-26 ··· | Strong S = weak S ? |
| 11-27 ··· | Add S + 0.25 to degree-strong eye |
| 11-28 ··· | Easy to see ? |
| 11-29 ··· | S < binocular completely corrected degree S ? |
| 11-30 ··· | Add S − 0.25 to both eyes |

FIG. 19 (b)

| | |
|---|---|
| 11-1 ··· | Type of anisometropia |
| 11-2 ··· | Initial spectacles wear ? |
| 11-3 ··· | Initial spectacles wear ? |
| 11-4 ··· | Initial spectacles wear ? |
| 11-5 ··· | Effect $\Delta C1$ subtraction process on both eyes based on table C with degree-strong eye as reference |
| 11-6 ··· | Set both eyes to S1' based on table A with degree-weak eye as reference |
| 11-7 ··· | Add S - 0.75 to degree-strong eye |
| 11-8 ··· | Effect $\Delta C2$ subtraction process on both eyes based on table D with degree-strong eye as reference |
| 11-9 ··· | Set degree-weak eye to degree reduced by $\Delta S2$ based on table B |
| 11-10 ··· | Add S - 0.75 to previous degree of degree-stron eye or completely correct degree-strong eye |
| 11-11 ··· | Set both eyes to C1' based on table C with degree-weak eye as reference |
| 11-12 ··· | Add C - 0.75 to degree-strong eye |
| 11-13 ··· | Effect $\Delta S1$ subtraction process on both eyes based on table A with degree-strong eye as reference |

FIG. 19 (c)

| | |
|---|---|
| 11-14 ··· | Set degree-weak eye to degree reduced by $\Delta C2$ based on table D |
| 11-15 ··· | Add C - 0.75 to previous degree of degree-stron eye or completely correct degree-strong eye |
| 11-16 ··· | Effect $\Delta S2$ subtraction process on both eyes based on table B with degree-strong eye as reference |
| 11-17 ··· | Set both eyes to C1' based on table C with degree-weak eye as reference |
| 11-18 ··· | Add C - 0.75 to degree-strong eye |
| 11-19 ··· | Set both eyes to S1' based on table A with degree-weak eye as reference |
| 11-20 ··· | Add S - 0.75 to degree-strong eye |
| 11-21 ··· | Set degree-weak eye to degree reduced by $\Delta C2$ based on table D |
| 11-22 ··· | Add C - 0.75 to previous degree of degree-stron eye or completely correct degree-strong eye |
| 11-23 ··· | Set degree-weak eye to degree reduced by $\Delta S2$ based on table B |
| 11-24 ··· | Add S - 0.75 to previous degree of degree-stron eye or completely correct degree-strong eye |

FIG. 20 (b)

| | |
|---|---|
| 12-1 ··· | Type of anisometropia |
| 12-2 ··· | Initial spectacles wear ? |
| 12-3 ··· | Initial spectacles wear ? |
| 12-4 ··· | Initial spectacles wear ? |
| 12-5 ··· | $C \leqq -0.5$ |
| 12-6 ··· | Effect $\Delta C1$ subtraction process on both eyes based on table C with degree-strong eye as reference |
| 12-7 ··· | Add $\Delta C1/2$ to binocular equivalent spherical surface S |
| 12-8 ··· | Add S + 0.75 to degree-strong eye |
| 12-9 ··· | Add C/2 to equivalent spherical surface S |
| 12-10 ··· | Add S + 0.75 to degree-strong eye |
| 12-11 ··· | $C \leqq -0.5$ |
| 12-12 ··· | Effect $\Delta C2$ subtraction process on both eyes based on table D with degree-strong eye as reference |
| 12-13 ··· | Add $\Delta C2/2$ to binocular equivalent spherical surface S |
| 12-14 ··· | Add S + 0.75 to previous degree of degree-stron eye or completely correct degree-strong eye |
| 12-15 ··· | Astigmatism exists in previous spectacles ? |
| 12-16 ··· | Add C/2 to equivalent spherical surface S |
| 12-17 ··· | Add S + 0.75 to previous degree of degree-stron eye or completely correct degree-strong eye |

FIG. 20 (c)

| | |
|---|---|
| 12-18 ··· | Set both eyes to C1' based on table C with degree-weak eye as reference |
| 12-19 ··· | Add Δ C1/2 to binocular equivalent spherical surface S |
| 12-20 ··· | Add C - 0.75 to degree-strong eye |
| 12-21 ··· | Set degree-weak eye to degree reduced by Δ C2 based on table D |
| 12-22 ··· | Add Δ C2/2 to binocular equivalent spherical surface S |
| 12-23 ··· | Add C - 0.75 to previous degree of degree-stron eye or completely correct degree-strong eye |
| 12-24 ··· | Set both eyes to C1' based on table C with degree-weak eye as reference |
| 12-25 ··· | Add Δ C1/2 to binocular equivalent spherical surface S |
| 12-26 ··· | Add C - 0.75 to degree-strong eye |
| 12-27 ··· | Add S + 0.75 to degree-strong eye |
| 12-28 ··· | Set degree-weak eye to degree reduced by Δ C2 based on table D |
| 12-29 ··· | Add Δ C2/2 to binocular equivalent spherical surface S |
| 12-30 ··· | Add C - 0.75 to previous degree of degree-stron eye or completely correct degree-strong eye |
| 12-31 ··· | Add S + 0.75 to previous degree of degree-stron eye or completely correct degree-strong eye |

FIG. 21 (b)

| | |
|---|---|
| 13-1 ··· | Type of anisometropia |
| 13-2 ··· | Initial spectacles wear ? |
| 13-3 ··· | Initial spectacles wear ? |
| 13-4 ··· | Initial spectacles wear ? |
| 13-5 ··· | $C \leqq -0.5$ |
| 13-6 ··· | Effect $\Delta$ C1 subtraction process on both eyes based on table C with degree-strong eye as reference |
| 13-7 ··· | Set both eyes to S1' based on table A with degree-weak eye as reference |
| 13-8 ··· | Add S − 0.75 to degree-strong eye |
| 13-9 ··· | Hold spherical surface as it is |
| 13-10 ··· | Set both eyes to S1' based on table A with degree-weak eye as reference |
| 13-11 ··· | Add S − 0.75 to degree-strong eye |
| 13-14 ··· | $C \leqq -0.5$ |
| 13-15 ··· | Effect $\Delta$ C2 subtraction process on both eyes based on table D with degree-strong eye as reference |
| 13-16 ··· | Set degree-weak eye to degree reduced by $\Delta$ S2 based on table B |
| 13-17 ··· | Add S − 0.75 to previous degree of degree-stron eye or completely correct degree-strong eye |
| 13-18 ··· | Astigmatism exists in previous spectacles ? |
| 13-19 ··· | Hold spherical surface as it is |
| 13-20 ··· | Set degree-weak eye to degree reduced by $\Delta$ S2 based on table B |

FIG. 21 (c)

| | |
|---|---|
| 13-21 ··· | Add S − 0.75 to previous degree of degree-stron eye or completely correct degree-strong eye |
| 13-22 ··· | Set both eyes to C1' based on table C with degree-weak eye as reference |
| 13-23 ··· | Add C − 0.75 to degree-strong eye |
| 13-24 ··· | Effect Δ S1 subtraction process on both eyes based on table A with degree-strong eye as reference |
| 13-25 ··· | Set degree-weak eye to degree reduced by Δ C2 based on table D |
| 13-26 ··· | Add C − 0.75 to previous degree of degree-stron eye or completely correct degree-strong eye |
| 13-27 ··· | Effect Δ S2 subtraction process on both eyes based on table B with degree-strong eye as reference |
| 13-28 ··· | Set both eyes to C1' based on table C with degree-weak eye as reference |
| 13-29 ··· | Add C − 0.75 to degree-strong eye |
| 13-30 ··· | Set both eyes to S1' based on table A with degree-weak eye as reference |
| 13-31 ··· | Add S − 0.75 to degree-strong eye |
| 13-32 ··· | Set degree-weak eye to degree reduced by Δ C2 based on table D |
| 13-33 ··· | Add C − 0.75 to previous degree of degree-stron eye or completely correct degree-strong eye |
| 13-34 ··· | Set degree-weak eye to degree reduced by Δ S2 based on table B |
| 13-35 ··· | Add S − 0.75 to previous degree of degree-stron eye or completely correct degree-strong eye |

FIG. 22 (b)

| | |
|---|---|
| 12-32 ··· | Physical disorder ? |
| 12-33 ··· | Add C + 0.25 to both eyes or vary AXIS |
| 13-36 ··· | Physical disorder ? |
| 13-37 ··· | Add C + 0.25 to both eyes or vary AXIS |

FIG. 23 (b)

| | |
|---|---|
| 14-1 ··· | Confirm binocular vision |
| 14-2 ··· | Determine prescribed values for far sight |
| 14-3 ··· | Presbyopia ? |
| 14-4 ··· | Return both eyes to binocular completely-corrected values and measure additive degrees for both eyes |
| 14-5 ··· | Additive degree = 0 ? |
| 14-6 ··· | Convert S difference between each binocular completely-corrected value and each value adjusted by calculation of prescribed values for far sight and C equivalent spherical difference into additive degrees and regard the converted degrees as degrees for near sight |
| 14-7 ··· | Visual acuity $\geq$ 0.7 ? |
| 14-8 ··· | Confirm visual acuity |
| 14-9 ··· | Add S + 0.25 to both eyes |
| 14-10 ··· | Visual acuity UP ? |
| 14-11 ··· | Add S − 0.25 to both eyes |
| 14-12 ··· | Initial spectacles wear ? |
| 14-13 ··· | Add S − 0.25 to both eyes |

FIG. 24 (b)

| | |
|---|---|
| 15-1 ··· | Confirm binocular vision |
| 15-2 ··· | Determine prescribed values for far sight |
| 15-3 ··· | Presbyopia ? |
| 15-4 ··· | Return both eyes to binocular completely-corrected values and measure additive degree at each eye |
| 15-5 ··· | Additive degree = 0 ? |
| 15-6 ··· | Convert S difference between each binocular completely-corrected value and each value adjusted by calculation of prescribed values for far sight and C equivalent spherical difference into additive degrees and regard the converted degrees as degrees for near sight |
| 15-7 ··· | Physical disorder ? |
| 15-8 ··· | Hold additive degree for degree-weak eye having S for far sight as it is and allow other eye to approach degree for degree-weak eye |
| 15-9 ··· | Physical disorder ? |
| 15-10 ··· | Visual acuity $\geq$ 0.7 ? |
| 15-11 ··· | Confirm visual acuity |
| 15-12 ··· | Add S + 0.25 to both eyes |
| 15-13 ··· | Visual acuity UP ? |
| 15-14 ··· | Add S - 0.25 to both eyes |
| 15-15 ··· | Difference in additive degree between R and L $\leq$ 0.25 ? |
| 15-16 ··· | Progressive multifocal lens is unavailable and use monofocal lens or bifocal lens |
| 15-17 ··· | Initial spectacles wear ? |
| 15-18 ··· | Add S - 0.25 to both eyes |

OPHTHALMIC APPARATUS

BACKGROUND OF THE INVENTION

1. Field of the Invention

The present invention relates to an ophthalmic apparatus, and more specifically to an ophthalmic apparatus suitable for corrective prescription of eyes to be examined, which are defective in refraction.

2. Description of the Related Art

It is important that the state of refraction of eyes to be examined is accurately examined to correct refractive ametropy or abnormalities of the eyes and thereby suitable degrees which provide no physical disorder and fatigue upon loading of spectacles, are prescribed in consideration of an appeal of a person to be examined, the degrees of previous spectacles, etc.

A completely correcting refractive power inspection is normally performed based on examined data about measurements or the like of the degrees of the previous spectacles by an objective test or inspection using a so-called refractometer or by a lens meter. The completely correcting refractive power inspection uses a subjective refractive power inspecting device for placing optical elements having various optical characteristics in their corresponding inspection windows by switching. The refractive power inspecting device obtains a response to the condition of visibility of a presented object from the person to be examined thereby to determine corrected degrees capable of obtaining the maximum vision.

In recent years, the examiner, which has little knowledge about and experience in optometry, was also becoming able to easily measure the completely correcting refractive power by organically coupling the subjective refractive power inspecting device, an object indicating device, etc. to one another and bringing an inspection procedure into a program.

However, a procedure for adjusting completely-corrected degrees after they have been obtained thereby to produce or obtain suitable prescribed values greatly depends on the examiner's knowledge and experience. A person having little experience in and unfamiliar to the optometry holds hard even now.

A problem arises that much time is normally required to obtain prescribed values and there is an individual difference in prescribed value among examiners.

SUMMARY OF THE INVENTION

With the foregoing in view, it is therefore an object of the present invention to provide an ophthalmic apparatus capable of easily obtaining suitable prescribed values even by an examiner having little experience in and unfamiliar to the optometry.

According to one aspect of the present invention, for achieving the above object, there is provided an ophthalmic apparatus for obtaining a refractive corrected-degree based on a refractive power of each of eyes to be examined, the ophthalmic apparatus comprises a refractive power inspecting means for inspecting the refractive power of the each eye, a program storing means for storing therein a program for measuring completely-corrected degrees of the eyes, adjusting the completely-corrected degrees according to factors for adjusting degrees to be corrected and thereby predicting degrees to be prescribed, an input means for inputting data about the factors for adjusting the degrees to be corrected, a program conducting means for advancing the program stored in the program storing means, a control means for sequentially activating the ophthalmic apparatus in accordance with the program and processing the result of inspection by completely-corrected degree inspecting means and the data input by the input means thereby to predict prescribed degrees, and a display means for displaying the prescribed degrees predicted by the control means.

An ophthalmic apparatus for obtaining a refractive corrected-degree based on a refractive power of each of eyes to be examined of this second invention, comprises a subjective refractive power inspecting device for inspecting a subjective refractive power of the each eye, an object indicating device for presenting an object for a visual acuity test an objective refractive power inspecting device used for an objective test, a program storing means for storing therein a program for measuring completely-corrected degrees of the eyes, adjusting the completely-corrected degrees according to factors for adjusting degrees to be corrected and thereby predicting degrees to be prescribed, an input means for inputting data about the factors for adjusting the degrees to be corrected, a program conducting means for advancing the program stored in the program storing means, a control means for activating the object indicating device and the subjective refractive power inspecting device in accordance with the program and processing the result of inspection by completely-corrected degree inspecting means and the data input by the input means thereby to predict degrees to be prescribed, and a display means for displaying the prescribed degrees predicted by the control means.

An ophthalmic apparatus for obtaining prescribed degrees of eyes to be examined of this third invention, comprises a program storing means for storing therein a program for measuring completely-corrected degrees of the eyes, adjusting the completely-corrected degrees according to factors for adjusting degrees to be corrected and thereby predicting degrees to be prescribed, a first input means for inputting data based on the refractive power inspection of the each eye, a second input means for inputting data about the factors exclusive of the result of refractive power inspection, a program conducting means for advancing the program stored in the program storing means, a control means for processing the data input by the first input means and the second input means in accordance with the program thereby to predict prescribed degrees, and a display means for displaying the prescribed degrees predicted by the control means.

The control means includes a storing means for storing therein quantities of correction based on degrees of near sightedness and astigmatism.

The control means stores therein correction quantities varied according to the presence or absence of the history of use of a refraction correcting device and the data input by the input means shows the presence or absence of the refraction correcting device.

The program has different correcting procedures each including at least one of the presence or absence of anisometropia, astigmatism and oblique astigmatism and either far sightedness or near sightedness as an element.

The apparatus further includes a display means for describing operational procedures of an examiner, which displays procedures necessary for respective steps pursuant to the program.

According to the present invention as described above, even an examiner having little experience in and unfamiliar to the optometry can easily obtain prescribed degrees suitable for each person to be examined.

The above and other objects, features and advantages of the present invention will become apparent from the following description and the appended claims, taken in conjunction with the accompanying drawings in which a preferred embodiment of the present invention is shown by way of illustrative example.

BRIEF DESCRIPTION OF THE DRAWINGS

The invention will be described with reference to the accompanying drawings wherein:

FIG. 4 is a view showing an case history screen displayed on a display;

FIGS. 8(a) and 8(b) are views for describing a prescribed-degrees control table list;

FIGS. 9(a) and 9(b) are views for describing another prescribed-degrees control table list;

FIGS. 10(a) and 10(b) are flowcharts for describing a corrected-degrees control program;

FIGS. 11(a) and 11(b) are flowcharts for describing a routine procedure in the corrected-degrees control program at the time that neither anisometropia nor astigmatism exists (hypermetropa or near sightedness exists);

FIGS. 12(a) and 12(b) are flowcharts for describing a routine procedure in the corrected-degrees control program at the time that the astigmatism exists but no oblique astigmatism exists exclusive of anisometropia (hypermetropa or near sightedness exists);

FIGS. 13(a) and 13(b) are flowcharts for describing a routine procedure in the corrected-degrees control program at the time that no anisometropia exists but the oblique astigmatism exists and the hypermetropa exists;

FIGS. 17(a)–17(c) are flowcharts for describing a routine procedure in the corrected-degrees control program at the time that the anisometropia and the astigmatism exist (but no oblique astigmatism exists) and the hypermetropa exists;

FIGS. 18(a) and 18(b) are flowcharts for describing a mode for selecting a fatigue reduction, a malaise or the like, of the corrected-degrees control program where the anisometropia, the astigmatism (exclusive of the oblique astigmatism) and the hypermetropa exist;

FIGS. 19(a)–19(c) are flowcharts for describing a routine procedure in the corrected-degrees control program at the time that the anisometropia and the astigmatism (exclusive of the oblique astigmatism) exist and the near sightedness exists;

FIGS. 20(a)–20 (c) are flowcharts for describing a routine procedure in the corrected-degrees control program at the time that the anisometropia and the oblique astigmatism exist and the hypermetropa exists;

FIGS. 23(a) and 23(b) are flowcharts for describing a routine procedure for determining prescribed values, of the corrected-degrees control program where no anisometropia exists;

DETAILED DESCRIPTION OF THE PREFERRED EMBODIMENTS

One embodiment of the present invention will hereinafter be described with reference to the accompanying drawings.

Figure 1:
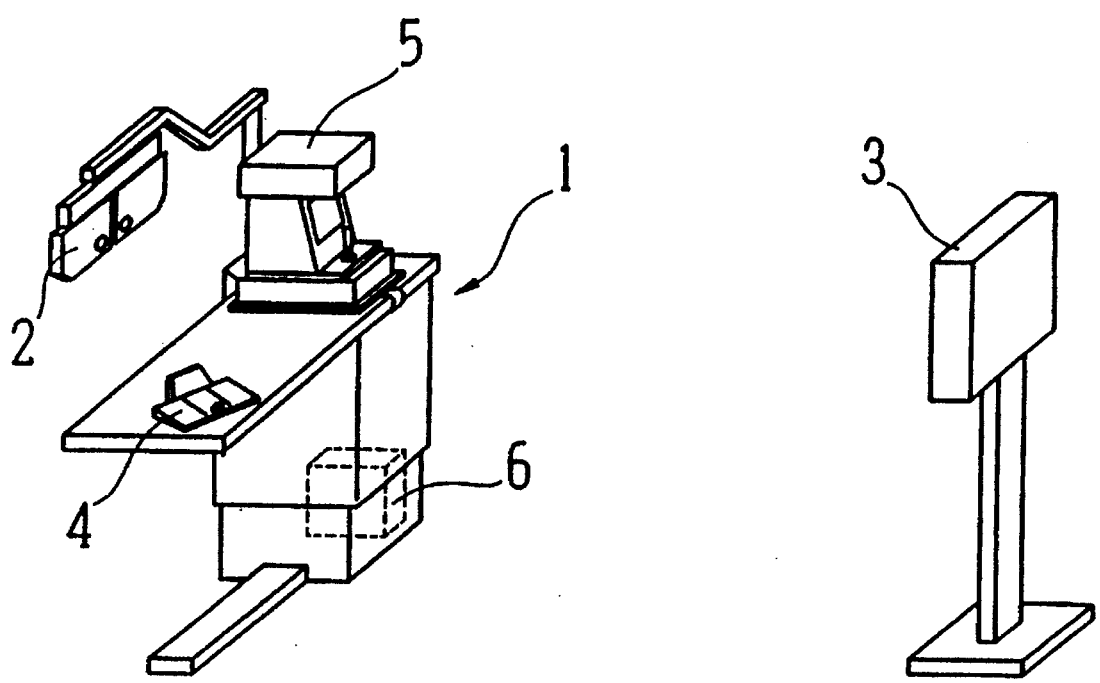
FIG. 1 is an external view showing a schematic configuration of an apparatus according to one embodiment of the present invention.

FIG. 1 is an external view schematically showing the structure of an apparatus according to the present embodiment. The ophthalmic apparatus according to the present embodiment roughly comprises an optometry table 1 placed in front of a person to be examined, a subjective refractive power inspecting device 2 for placing various optical devices or elements in left and right inspection windows by switching, a film-driven type object indicating device 3 for presenting an object for a visual acuity test, a controller 4 for performing switching between the optical elements placed in the inspection windows of the subjective refractive power inspecting device 2, switching between objects presented by the object indicating device 3, etc., an objective eye refractive power measuring device 5 mounted on a movable tray and slidable on the optometry table 1, and a relay unit 6 for performing a communication relay among the controller 4, the subjective refractive power inspecting device 2, the objective eye refractive power measuring device 5 and an unillustrated lens meter.

Figure 2:
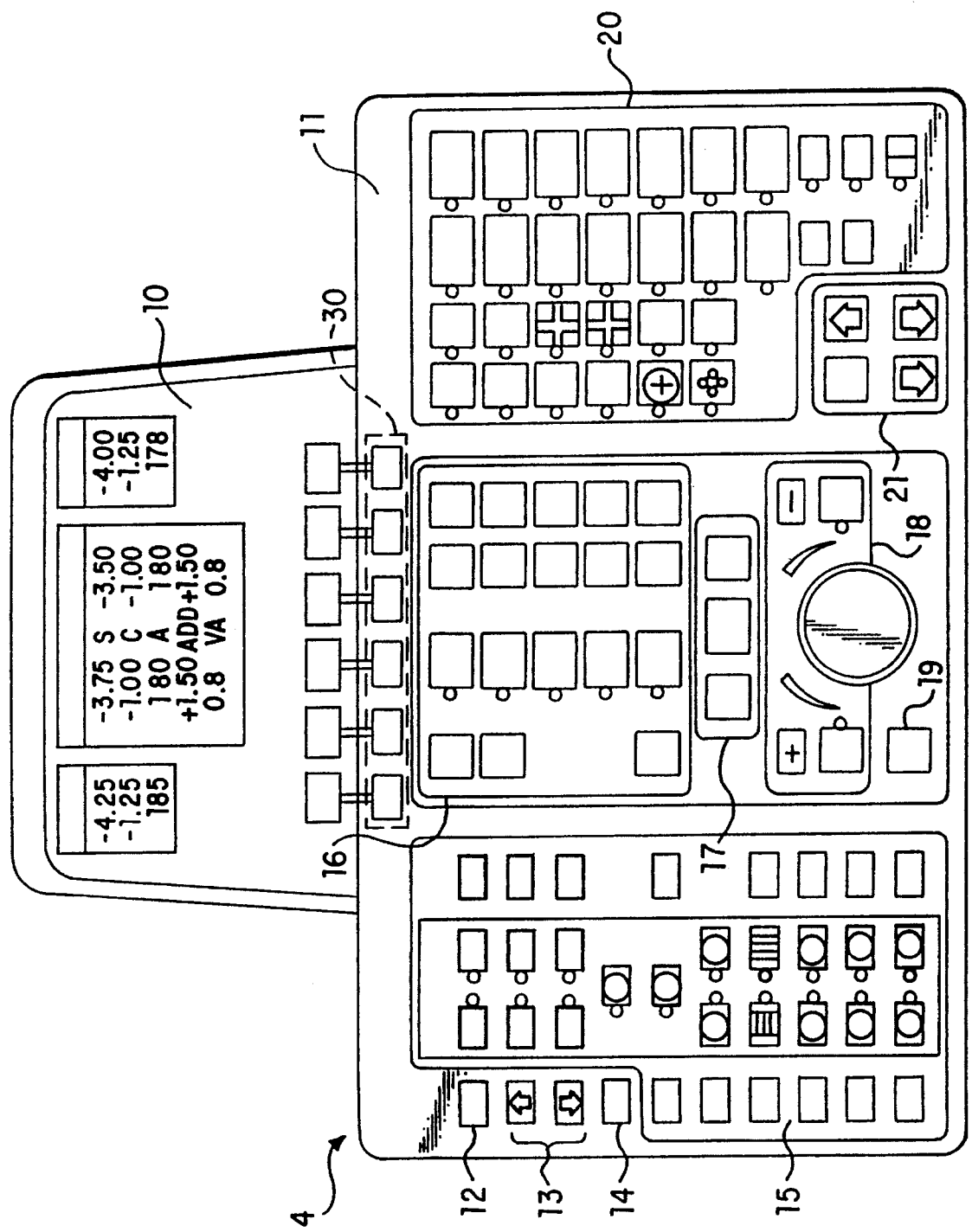
FIG. 2 is a view illustrating a controller shown in FIG. 1 as seen from above.

FIG. 2 is a view of the controller 4 as seen from above.

Reference numeral 10 indicates a display for displaying optometry information thereon. A dot matrix screen is used in the display 10 so that various information can be displayed thereon by switching.

Reference numeral 11 indicates a switch unit. A menu switch 12 for switching a display screen of the display 10 to a menu screen, two cursor movement switches 13 for moving a cursor displayed on the screen, an execution switch 14, an auxiliary lens switch group 15 for driving an optical system of the subjective refractive power inspecting device 2, a measurement mode changeover switch group 16, a measuring eye designation switch group 17, an input switch group 18 having switches used for inputting numerical values and a knob switch, a shift switch 19 used in combination with other switches, an object switch group 20 for driving the object indicating device 3, a program execution switch group 21 having a start switch for executing program optometry and a program feed switch, and a screen-correspondence switch group 30 provided so as to correspond to information displayed in predetermined positions below the screen of the display 10.

Figure 3:
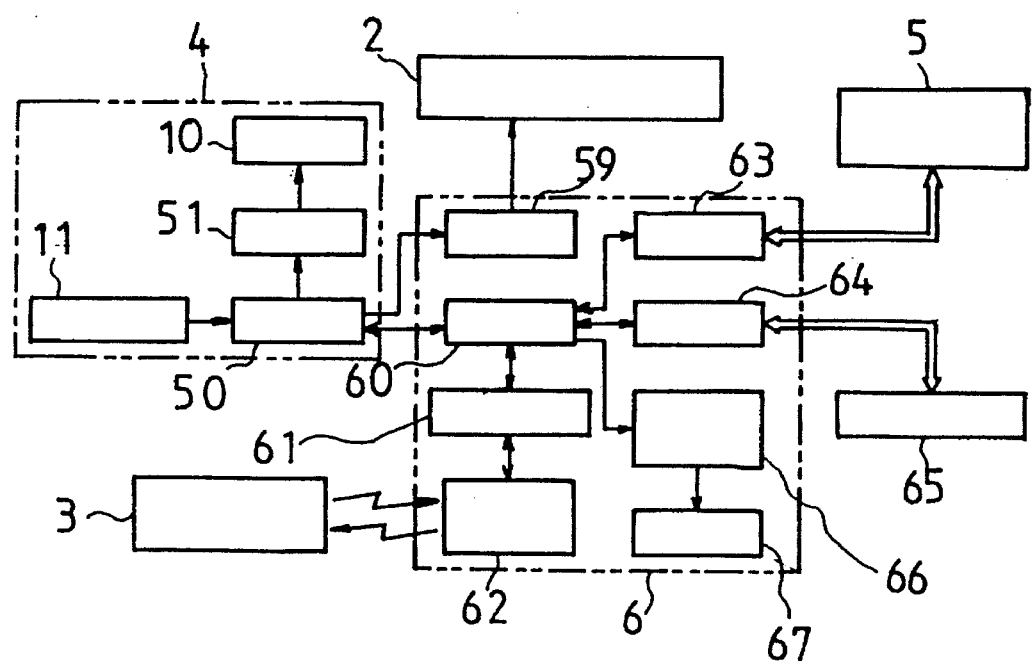
FIG. 3 is a block diagram for describing the control of the apparatus shown in FIG. 1.

FIG. 3 is a block diagram for describing the control of the apparatus.

Switch signals outputted from the switch unit 11 of the controller 4 are subjected to predetermined processing, followed by input to a control circuit 50. The control circuit 50 changes the switch signals into various data respectively and thereafter sends the same to the relay unit 6. Data about the refractive power is sent to the subjective refractive power inspecting device 2 through a relay circuit 59 and a control circuit of the subjective refractive power inspecting device 2 places a predetermined optical element in its corresponding inspection window. Further, data about an object is sent to the object indicating device 3 through a control circuit 60 and an input/output circuit 61. Communications between the relay unit 6 and the object indicating device 3 are performed using optical signals through an optical-signal receiving and emitting section 62 of the relay unit 6 and an optical-signal receiving and emitting section of the object indicating device 3. However, the communications may be carried out by cables.

The control circuit 60 is electrically connected to the objective eye refractive power measuring device 5 and the lens meter 65 through communication circuits 63 and 64. The control circuit 60 transfers these measured data to the controller 4. A printer 67 is electrically connected to the control circuit 60 through a printer drive circuit 66 so as to output and print various measured data.

Further, the control circuit 50 is responsive to the signals from the relay unit 6 and the switch unit 11 to allow their optometry information to be displayed on the display 10 through a display circuit 51.

An optometry operation of the apparatus having the above-described structure will be described based on flowcharts.

A normal optometry procedure is carried out in order of case history, a preliminary inspection (including a naked eye vision measurement, a correction vision measurement, an interpupillary distance measurement, a dominant eye detection, etc.), an objective inspection, a subjective inspection, a temporary-frame or centering inspection and a prescribed value decision. However, steps up to the calculation of completely-corrected values by the case history, the preliminary inspection, the objective inspection and the subjective inspection will be briefly described herein. Thereafter, a step for obtaining prescribed values will be described in detail. An input completion switch for each step may be shared for the transition from each of the steps up to the calculation of the completely-corrected values by the case history, the preliminary inspection, the objective inspection and the subjective inspection to the next step. Alternatively, a switch (menu selection) for the transition of the corresponding step to the next step may be provided.

Case History

The menu switch 12 of the controller 4 is depressed to select an/Case history/entry from various function menus with the cursor movement switch 13. When the execution switch 14 is depressed, an case history screen shown in FIG. 4 is displayed on the display 10. An inspector or examiner inquires of a person to be examined a purpose for preparing spectacles or the like, age, male or female, occupation, hobby, history of spectacles, history of a contact lens, etc. in accordance with the case history entry. Further, the examiner operates the cursor movement switch 13 and the knob switch to input the respective items. Finally, the examiner depresses the execution switch 14 to complete their input.

Preliminary Inspection

The preliminary inspection includes a naked eye vision measurement, a previous spectacles correction vision measurement, an interpupillary distance measurement, a dominant eye detection, etc.

Upon the naked eye vision measurement, a naked-eye switch of the measurement mode changeover switch group 16 is depressed to switch the screen displayed on the display 10 to an unaided vision input screen. The vision of the person to be examined is measured by changing the object of the object indicating device 3 under the operation of the object switch group 20 while the examiner is obtaining an answer from the person to be examined and the measured values of vision are inputted via the input switch group 21 or the like.

The previous spectacles correction vision measurement is carried out as follows. When the person to be examined puts on spectacles, an input switch and a previous spectacles switch of the measurement mode changeover switch group 16 are pressed so that data measured by the lens meter 65 can be transferred to the control circuit 50. The control circuit 50 allows a memory provided therein to store the transferred data about the degree of lenses. The control circuit 50 switches the display screen to the previous spectacles vision input screen (not shown) so as to display the stored data about the degree of the left and right lenses. The previous spectacles correction vision measurement is performed in a manner similar to the naked eye vision measurement.

The interpupillary distance measurement is carried out by using an unillustrated interpupillary distance apparatus finder or the like or an interpupillary distance measuring mechanism of the objective eye refractive power measuring device 5. Data measured by the interpupillary distance apparatus or the like is input in a state in which a PD switch of the measurement mode changeover switch group 16 has been depressed and the screen displayed on the display 10 has been changed to an interpupillary distance input screen. Data measured by the interpupillary distance measuring mechanism of the objective eye refractive power measuring device 5 is input together with data obtained upon the objective inspection to be described later by depressing the input switch and an objective value switch of the measurement mode changeover switch group 16.

Figure 5:
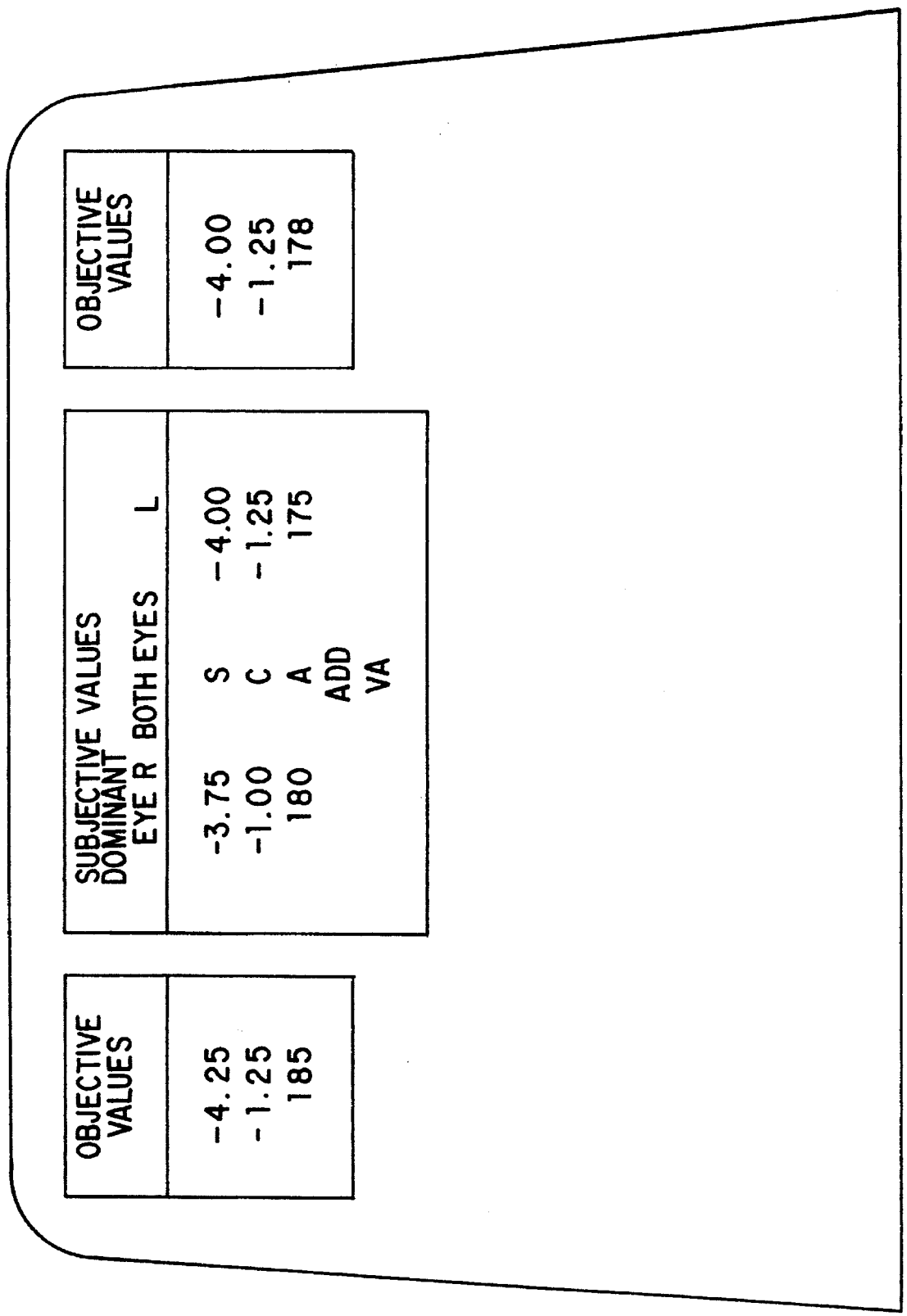
FIG. 5 is a view illustrating a display screen on which the result of objective test is inputted.

The dominant eye detection can be performed by a perforated card process or a Rosenbach process or the like. The result of detection is inputted by depressing either a R or L switch of the measuring eye designation switch group 17 while depressing the shift switch 19. The input dominant-eye information is stored in the control circuit 50 and is displayed as an /dominant eye/ at the side of either R or L in the screen displayed upon vision measurement (see FIG. 5).

Objective Inspection

The objective inspection is performed using the objective eye refractive power measuring device 5. Respective measured values of binocular spherical degrees (SPH), astigmatic degrees (CYL) and astigmatic axial angles (AXIS) are read by depressing the input switch and the objective value switch and stored in the memory of the control circuit 50. The control circuit 50 drives the optical system of the subjective refractive power inspecting device 2 based on the stored respective data thereby to place a lens associated with each measured value in its corresponding inspection window: The control circuit 50 switches the screen displayed on the display 10 to a screen shown in FIG. 5. A central portion of the displayed screen represents subjective values whereas left and right portions thereof represent objective values.

When the result of objective inspection is inputted to the control circuit 50, the control circuit 50 is automatically changed to a subjective value inspection mode (i.e., the control circuit 50 is brought into a state identical to a state in which a subjective value switch has been depressed).

Calculation of Completely-Corrected Values by Subjective Inspection

Upon the subjective inspection, the eyes are first completely corrected on a monocular basis. It is common for this measurement to finally perform a visual acuity test and calculate a monocular completely-corrected value after execution of a vision check, a red/green inspection, an astigmatic axis inspection, an astigmatic degree inspection based on the data obtained by the objective inspection and re-execution of the red/green inspection. In the apparatus according to the present embodiment, items for the respective inspections have been programmed into the control circuit 50. When each inspection is performed in accordance with the optometry program, the start switch of the program execution switch group 21 is depressed to start the optometry program. Thereafter, the program feed switch is depressed to issue operating signals necessary for inspections to the subjective refractive power inspecting device 2 and the object indicating device 3, followed by execution of the successive inspections.

Figure 6:
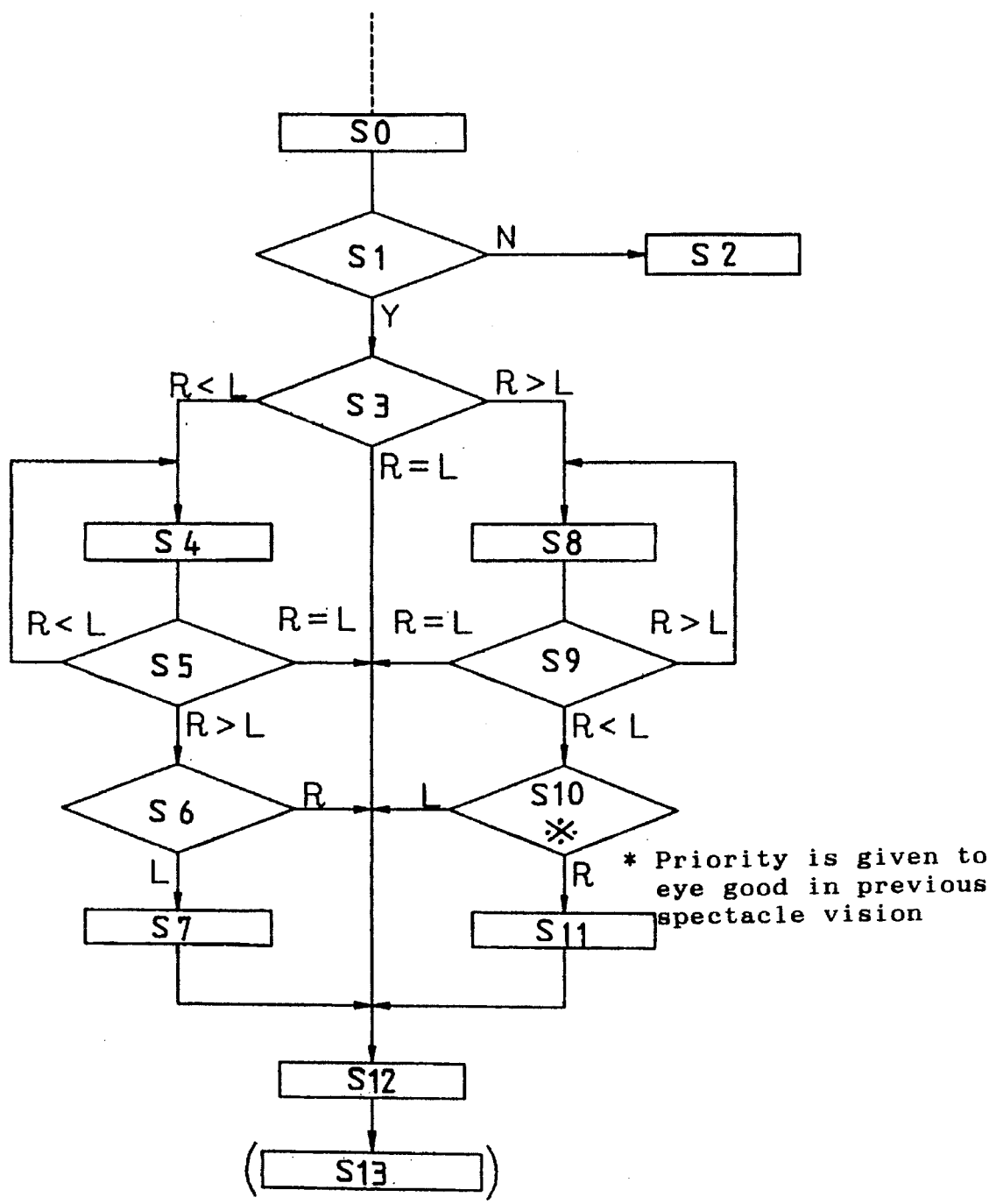
FIGS. 6(a) and 6(b) are flowcharts for describing a procedure for performing a binocular balance test.

After the monocular completely-corrected value has been obtained, a binocular balance is inspected to obtain binocular completely-corrected values (see a flowchart shown in FIGS. 6(a,b)). When the maximum visual acuity of a single eye is now less than 0.7, a comment indicative of the fact that the examiner urges the person to be examined to undergo a close examination, is displayed on the display 10.

When a difference in sight occurs in the monocular completely-corrected degrees upon the binocular balance test, a balance correction for adding S+0.25 D to a well-visible eye is executed. When the balance correction makes it hard to be visible to the corrected eye, a priority is given to the best previous spectacle vision. If a person first puts on spectacles, then a priority is given to his/her dominant eye. Since information about the dominant eye is always displayed on the display screen of the display, the examiner can judge it at first sight. When it is desired to recognize data about the previous spectacle vision, the data is displayed on the screen by depressing the previous spectacles switch.

Figure 7:
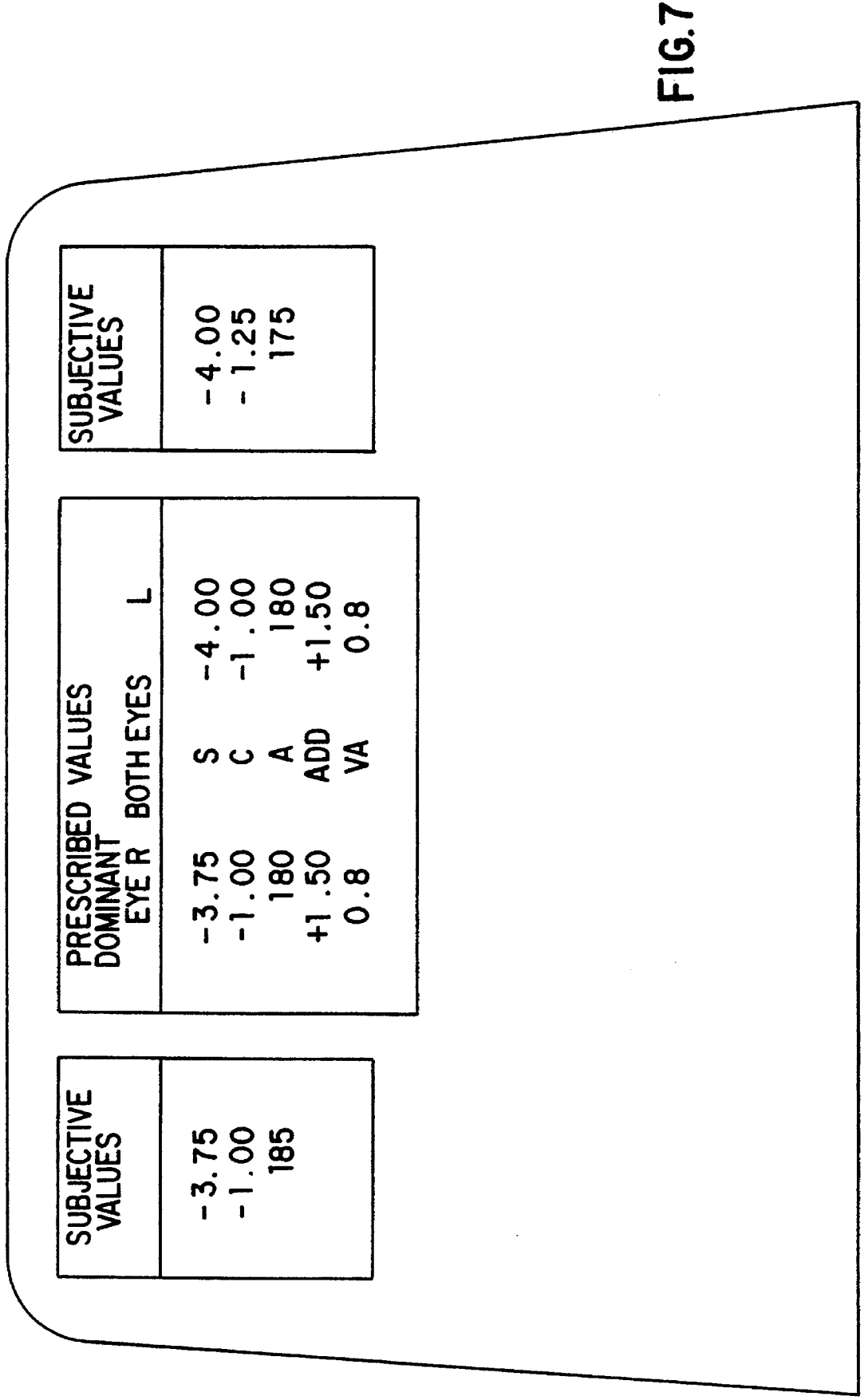
FIG. 7 is a view showing a display screen in a prescribed value mode.

Calculation of Prescribed Values by Subjective Inspection (1) After the binocular completely-corrected degrees have been obtained, the examiner proceeds to a corrective degree control inspection for determining prescribed values. When a prescribed value switch of the measurement mode changeover switch group 16 is depressed, the screen displayed on the display 10 is switched to a prescribed value mode (see FIG. 7). The present apparatus has a corrected-degrees control program for calculating controlled or adjusted degrees to be expected as most suitable for a person to be examined. Necessary operations are displayed on the display 10 so as to be notified to the examiner. Further, the control circuit 50 includes storage circuits having therein prescribed-degrees control table lists classified into four types shown in FIGS. 8(a,b) and 9(a,b). In FIGS. 8(a,b) and 9(a,b), a table A represents a table list applied to a person who is nearsighted and firstly puts on a initial spectacles wear, a table B represents a table list applied to a person who is nearsighted and already wears the spectacles or the like, a table C represents a table list applied to a person who is astigmatic and firstly puts on the spectacles, and a table D represents a table list applied to a person who is astigmatic and already wears the spectacles or the like.

The corrected-degrees control program is started by depressing the prescribed value switch while depressing the shift switch 19.

Figure 10A:
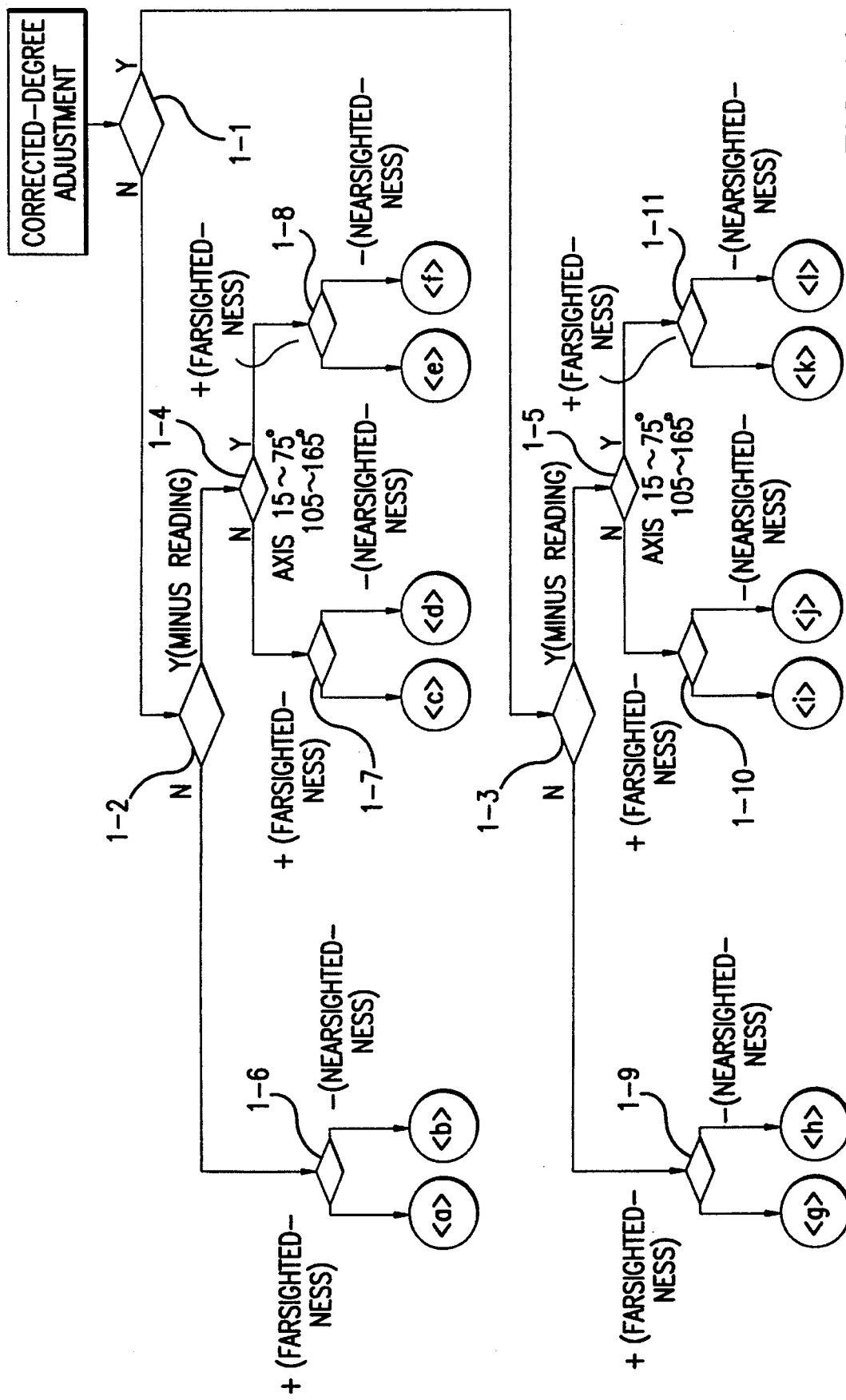

(2) As shown in FIGS. 10(a,b), the control circuit 50 firstly determines or judges based on the binocular completely-corrected value data stored in the memory whether anisometropia (if the difference in spherical degree or cylindrical degree between the left and right eyes is greater than or equal to 1.0 D, the anisometropia is regarded as being present in the present embodiment) (Step 1-1) exists, astigmatism exists (Steps 1-2 and 1-3), oblique astigmatism exists if the astigmatism exists (astigmatic axis falls within a range from 15 degrees to 75 degrees or a range from 105 degrees to 165 degrees) (Steps 1-4 and 1-5), and either farsightedness or nearsightedness exists (Steps 1-6 through 1-11). The control circuit 50 performs any of <a> through <l> based on the results of decision.

<a>

If it is judged at Step 1-6 that the farsightedness exists (neither the anisometropia nor the astigmatism exists), then the degree of spectacles remains at the completely-corrected degrees.

Figure 11A:
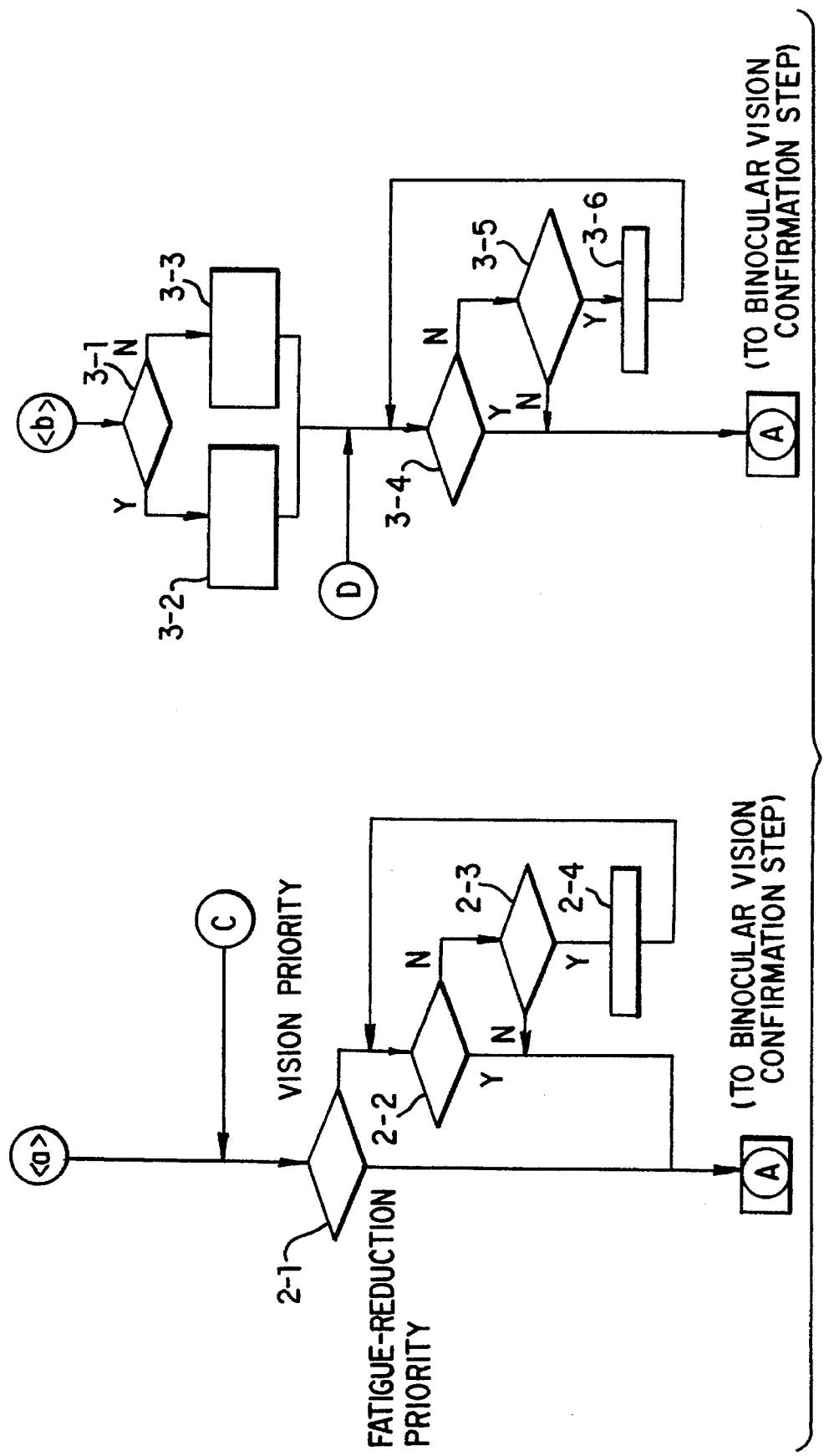

As shown in FIGS. 11(a,b), the examiner selects in accordance with the designation of a main appeal (Step 2-1) of the person to be examined, a decision made as to whether a priority should be given to the vision or a fatigue should be lessened, with a switch of the screen-correspondence switch group 30. If it is judged that the fatigue should be reduced, then the examiner proceeds to a binocular vision confirmation step to be described later. If it is judged that the priority should be given to the vision, then an easy-to-see confirmation is performed based on the presentation of an object (Step 2-2). The easy-to-see confirmation is carried out in the following manner. Namely, the control circuit 60 sends a signal to the object indicating device 3 through the optical-signal receiving and emitting section 62 and the object indicating device 3 presents a necessary object to the person to be examined. If the person finds to be satisfactory in visibility, then the examiner depresses the program feed switch and proceeds to the binocular vision confirmation step (to be described later). If the person finds to be hard to see, it is then confirmed whether the spherical degree S reaches minus (Step 2-3). After the spherical degree has been added to both eyes (Step 2-4), the easy-to-see confirmation operation at Step 2-2 is performed again. Since the spherical degree to be added can be set under the operation of the input switch group 18 and stepwise guides or indexes (up to six indexes at maximum) for prescribed values are displayed below the screen, the index can be selected by the screen-correspondence switch group 30. The indexes for the prescribed values are displayed at a 0.25 D step and are indicated within a range in which the spherical degree S is not rendered minus. After completion of such a step, the examiner depresses the program feed switch, followed by proceeding to the binocular vision confirmation step to be described later.

<b>

If it is judged at Step 1-6 that the near sightedness exists (neither the anisometropia nor the astigmatism exists), then the routine procedure proceeds as follows. As shown in FIGS. 11(a,b) in the same manner as described above, the control circuit 50 judges based on the case history whether the initial spectacles wear is performed (Step 3-1). If it is judged from data about the decision at Step 3-1 that the initial spectacles wear has been made, then the control circuit 50 adjusts the spectacle degrees to degrees obtained by effecting an arithmetic process (hereinafter called arithmetic process A) for respectively subtracting ΔS1 from the completely-corrected degrees based on the table A on both eyes with a degree-strong eye as reference (Step 3-2). If the answer is NO at Step 3-1, then the control circuit 50 adjusts the spectacle degrees to degrees obtained by effecting an arithmetic process (hereinafter called arithmetic process B) for respectively subtracting ΔS2 from the completely-corrected degrees based on the table B on both eyes with the degree-strong eye as reference (Step 3-3). The control circuit 50, which has calculated the controlled or adjusted degrees, issues instructions so that lenses associated with the degrees are placed in their corresponding inspection windows of the subjective refractive power inspecting device 2 and allows the degrees to be displayed on a prescription column of the display 10. The examiner confirms whether the adjusted degrees set to the subjective refractive power inspecting device 2 are easy to see (Step 3-4). If the answer is found to be NO at Step 3-4, it is then checked whether the adjusted degrees exceed the completely-corrected degrees (Step 3-5). If the answer is found to be YES at Step 3-5, then minus spherical degrees are added to both eyes (Step 3-6) and thereafter the easy-to-see inspection is executed again (since candidates for prescribed values are displayed below the screen, the inspection may be carried out based on them in the same manner as at Step 2-4 referred to above). If the person to be examined finds to be satisfactory in visibility or the adjusted degrees has reached the completely-corrected degrees, then the examiner depresses the program feed switch and proceeds to the binocular vision confirmation step.

<c>

Figure 12A:
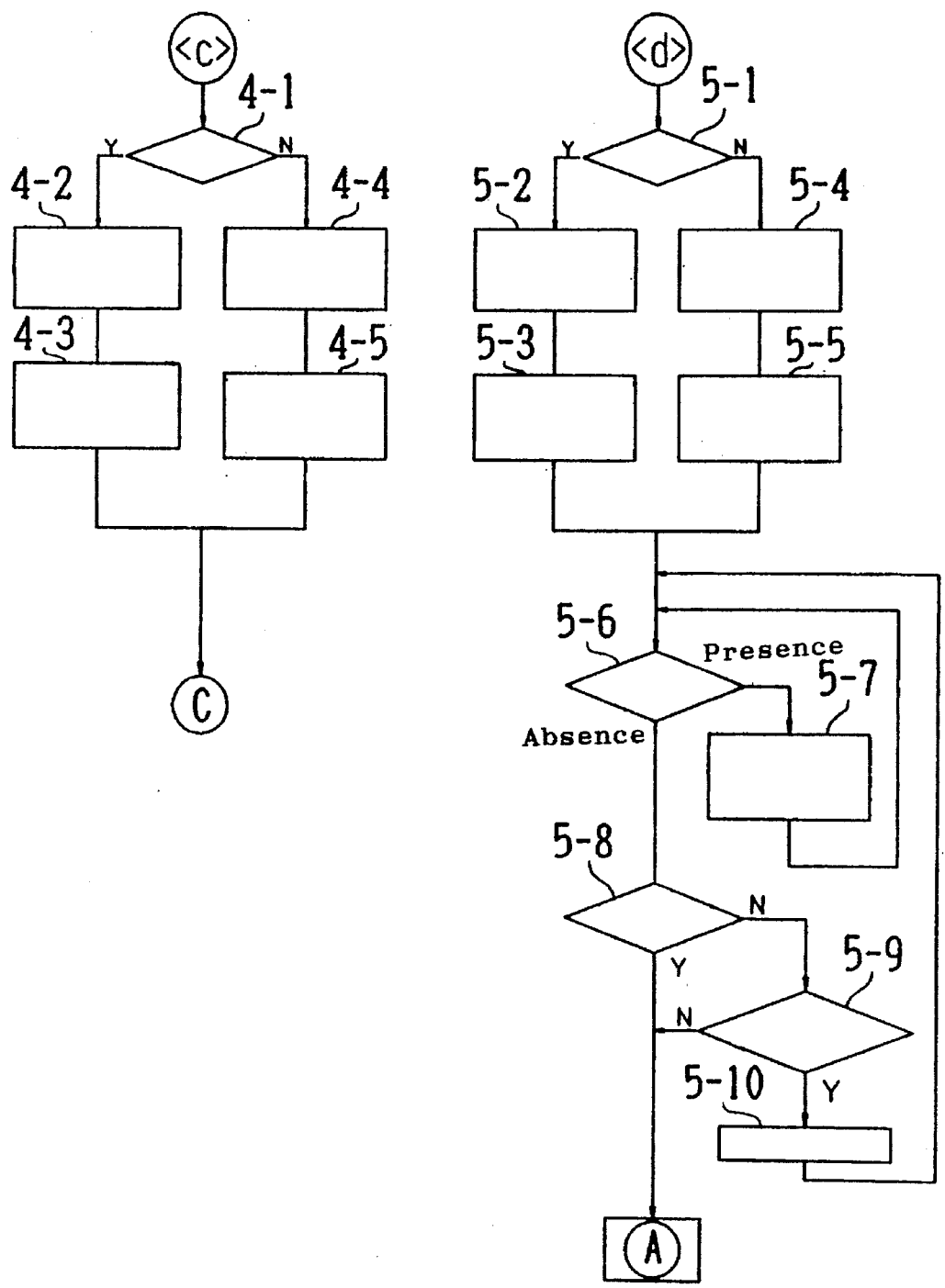

This shows the case where the farsightedness having the astigmatism exclusive of the oblique astigmatism exists (no anisometropia exists) at Step 1-7. As shown in FIGS. 12(a,b), the control circuit 50 judges based on the case history whether the initial spectacles wear is performed (Step 4-1). If the answer is found to be YES at Step 4-1, then the control circuit 50 effects, based on data about the decision (Step 4-1), an arithmetic process (hereinafter called arithmetic process C) for respectively subtracting ΔC1 from the completely-corrected astigmatic degrees C based on the table C on both eyes with an astigmatism-strong eye as reference (Step 4-2) and then adds ΔC1/2 to each of spherical degrees S of both eyes thereby to adjust the spectacle degrees to degrees leading to an equivalent spherical surface (Step 4-3).

If the answer is found to be NO (Step 4-1), then the control circuit 50 effects an arithmetic process (hereinafter called arithmetic process D) for respectively subtracting ΔC2 from the completely-corrected astigmatic degrees C based on the table D on both eyes with the astigmatism-strong eye as reference (Step 4-4) and then adds ΔC2/2 to each of spherical degrees S of both eyes thereby to adjust the spectacle degrees to degrees leading to an equivalent spherical surface (Step 4-5).

After the calculation of the adjusted degrees, the examiner proceeds to Step 2-1 referred to above in accordance with the screen display.

<d>

When the near sightedness having the astigmatism free of the oblique astigmatism exists (no anisometropia exists) at Step 1-7, the control circuit 50 judges as shown in FIGS. 12(a,b) whether the initial spectacles wear is performed (Step 5-1). If the answer is found to be YES at Step 5-1, then the control circuit 50 performs the arithmetic process C (Step 5-2) and the arithmetic process A (Step 5-3).

If the answer is found to be NO at Step 5-1, then the control circuit 50 performs the arithmetic process D (Step 5-4) and the arithmetic process B (Step 5-5). Further, the examiner confirms a physical disorder or malaise developed according to the adjusted degrees (Step 5-6). When the person to be examined complains of the physical disorder, C+0.25 D is added to the astigmatic degrees of both eyes or S+0.25 D is added to each of the spherical degrees of both eyes (Step 5-7). Since candidates for prescribed values are displayed below the screen, one of both adjustments can be selected by the screen-correspondence switch 30. When the confirmation of the physical disorder is completed, the control circuit 50 proceeds to an easy-to-see confirmation step (Step 5-8). When the person cannot obtain a satisfactory visible sense, a confirmation is made as to whether the adjusted spherical degrees exceed the completely-corrected degrees (Step 5-9). If the answer is found to be YES at Step 5-9, then Step 5-10 is executed but is identical to Steps 3-4 through 3-6.

<e>

Figure 13A:
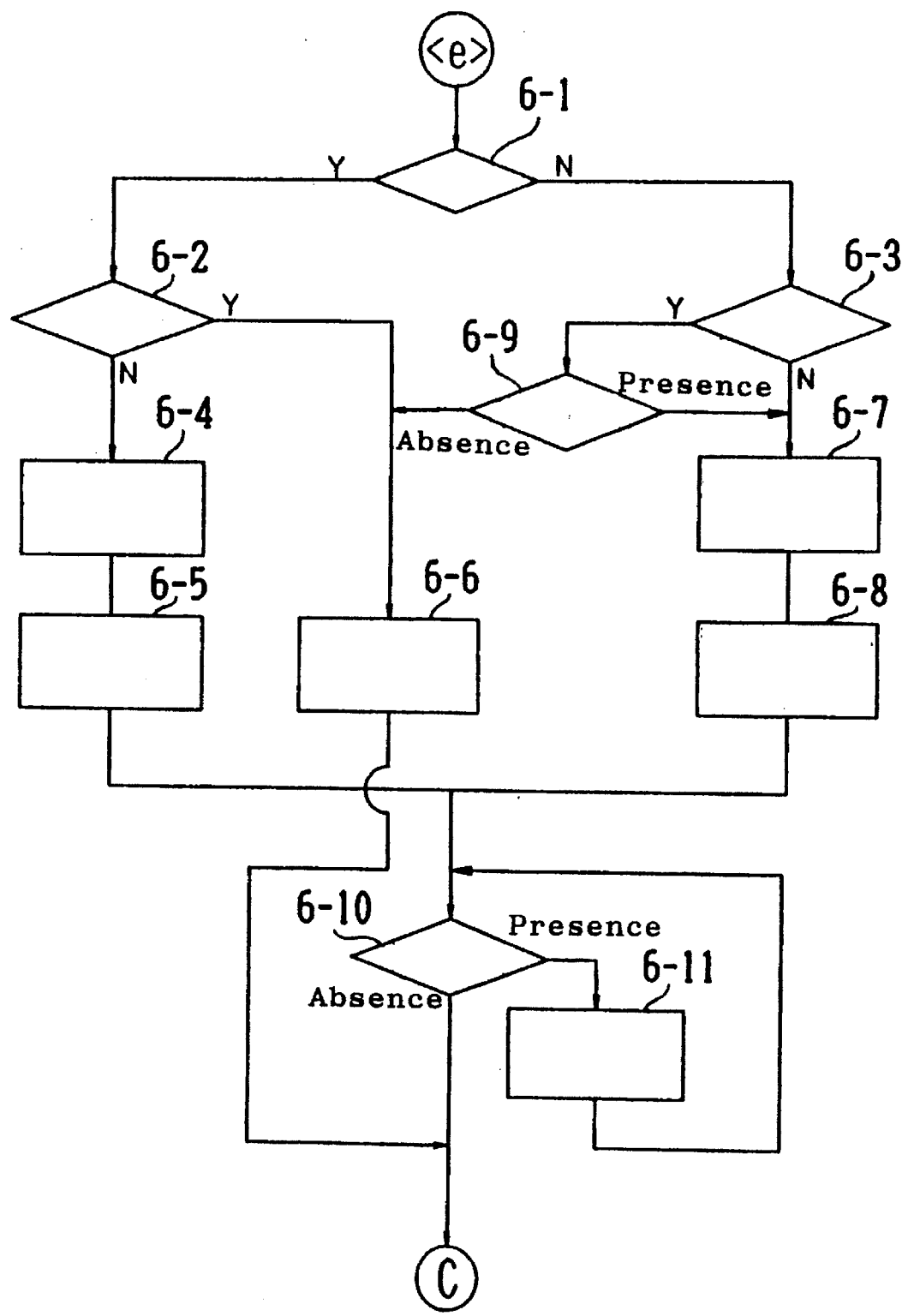

When the farsightedness having the oblique astigmatism exists (no anisometropia exists) at Step 1-8, the control circuit 50 judges as shown in FIGS. 13(a,b) whether an initial spectacles wear is performed (Step 6-1) and judges whether an astigmatic degree C is less than or equal to −0.5 D (Steps 6-2 and 6-3). If the answer is found to be YES at Step 6-1 and the astigmatic degree C exceeds −0.5 D, then the control circuit 50 performs the arithmetic process C (Step 6-4) and thereafter adds ΔC1/2 to a binocular spherical degree S to produce an equivalent spherical surface (Step 6-5), thereby calculating degrees to be adjusted. When the astigmatic degree C is less than or equal to −0.5 D, the astigmatism is regarded as negligible. In this condition, the control circuit 50 sets the astigmatic degree to 0 and adds one-half the reduced astigmatic degree to the spherical degree S to obtain an equivalent spherical surface (Step 6-6), thereby calculating degrees to be adjusted. If the answer is found to be NO at Step 6-1 and the astigmatic degree C exceeds −0.5 D, then the control circuit 50 performs the arithmetic process D (Step 6-7) and adds C/2 to the binocular spherical degree S to obtain an equivalent spherical surface (Step 6-8), thereby calculating degrees to be adjusted.

If it is determined from the decision at Step 6-3 that the astigmatic degree C is less than or equal to −0.5 D, then the control circuit 50 judges whether the astigmatism exists in the previous spectacles (Step 6-9). If the astigmatism is found to be nil, then the routine proceeds to Step 6-6 referred to above. If the astigmatism is found to exist, then the routine proceeds to Step 6-7 referred to above where degrees to be adjusted are calculated.

An examiner confirms a physical disorder of a person to be examined in accordance with instructions on the screen (Step 6-10). If the physical disorder is found to exist at Step 6-10, then C+0.25 D is added to both eyes or the astigmatic axis is varied (or both are varied) to execute a physical disorder confirmation process (Step 6-11). Since candidates for prescribed values are displayed below the screen even in this case, either one of both can be selected by the screen-correspondence switch 30. If the physical disorder is found not to exist at Step 6-10, then the examiner performs the easy-to-see confirmation at Step 2-1 referred to above and thereafter proceeds to the binocular vision confirmation step.

<f>

Figure 14:
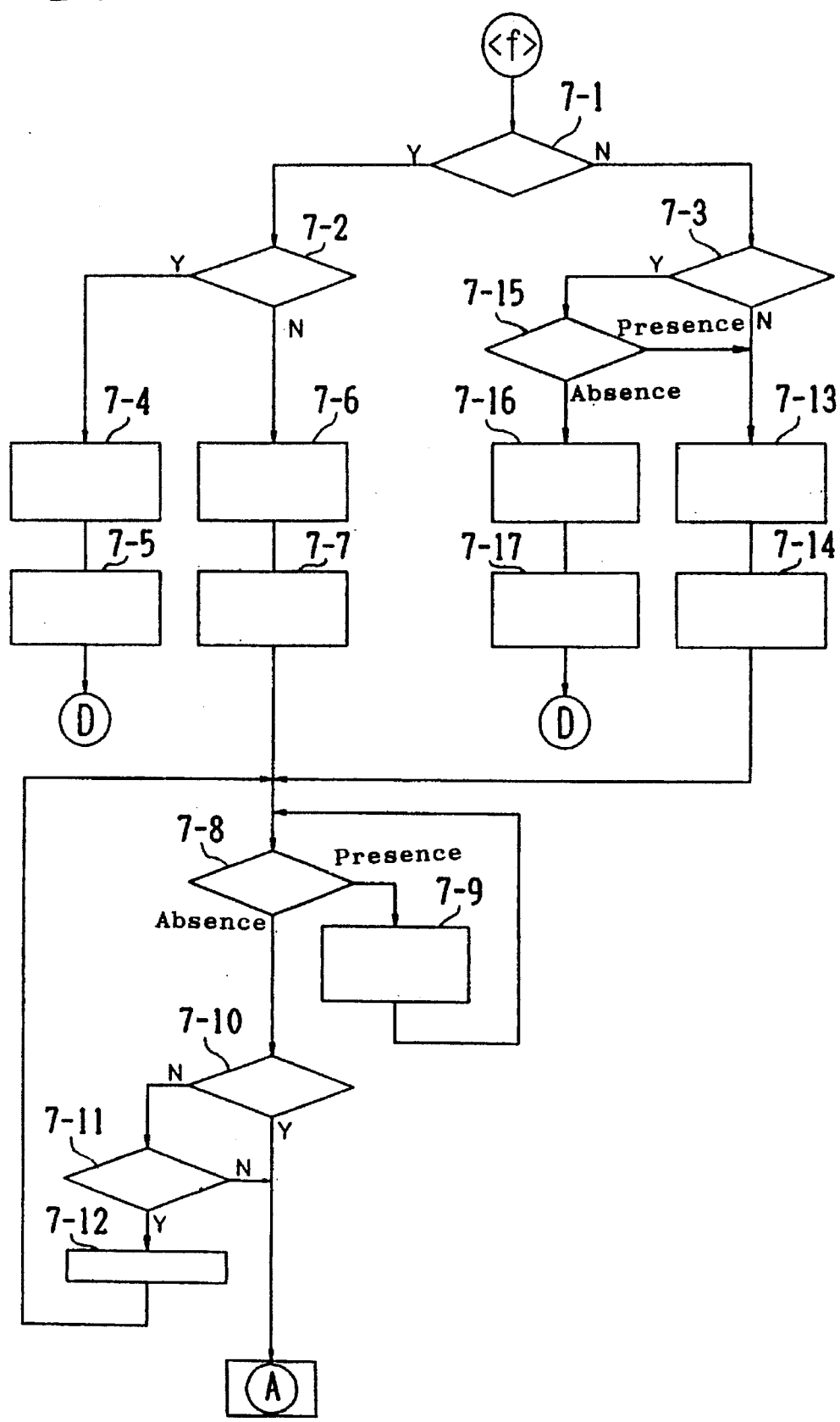
FIGS. 14(a) and 14(b) are flowcharts for describing a routine procedure in the corrected-degrees control program at the time that no anisometropia exists but the oblique astigmatism exists and the near sightedness exists.

When the near sightedness having the oblique astigmatism exists (no anisometropia exists) at Step 1-8, the control circuit 50 judges as shown in FIGS. 14(*a,b*) whether an initial spectacles wear is made (Step 7-1) and an astigmatic degree C is less than or equal to −0.5 D (Steps 7-2 and 7-3). If the answer is found to be YES and the astigmatic degree C is found to be less than or equal to −0.5 D, then the astigmatism is judged as negligible and hence the astigmatic degree is set to 0 (Step 7-4). Next, the control circuit 50 performs the arithmetic process A (Step 7-5). Thereafter, the examiner performs the easy-to-see confirmation at Step 3-4 referred to above and thereafter proceeds to the binocular vision confirmation step. If the astigmatic degree is found to exceed −0.5 D at Step 7-2, then degrees obtained by the arithmetic process C (Step 7-6) and the arithmetic process A (Step 7-7) are regarded as controlled or adjusted degrees. Further, the examiner confirms a physical disorder of a person to be examined (Step 7-8). If the physical disorder is found to exist at Step 7-8, then a process similar to Step 6-11 is executed (Step 7-9). Thereafter, the examiner performs an easy-to-see confirmation (Steps 7-10 through 7-12) and then proceeds to the binocular vision confirmation step.

If the answer is found to be NO at Step 7-1 and the astigmatic degree C is found to exceed −0.5 D, then the control circuit 50 performs the arithmetic process D (Step 7-13) and the arithmetic process B (Step 7-14). Thereafter, the examiner proceeds to Step 7-8 referred to above. If the astigmatic degree C is found to be less than or equal to −0.5 D at Step 7-3, then the control circuit 50 judges whether the astigmatism exists in the previous spectacles (Step 7-15). If the astigmatism is found not to exist at Step 7-15, then the astigmatic degree is set to 0 (Step 7-16) and degrees obtained by performing the arithmetic process B (Step 7-17) are regarded as adjusted degrees. Thereafter, the examiner performs the easy-to-see confirmation at Step 3-4 referred to above. If the astigmatism is found to exist at Step 7-15, then the examiner proceeds to Step 7-13 referred to above.

<g>

Figure 15:
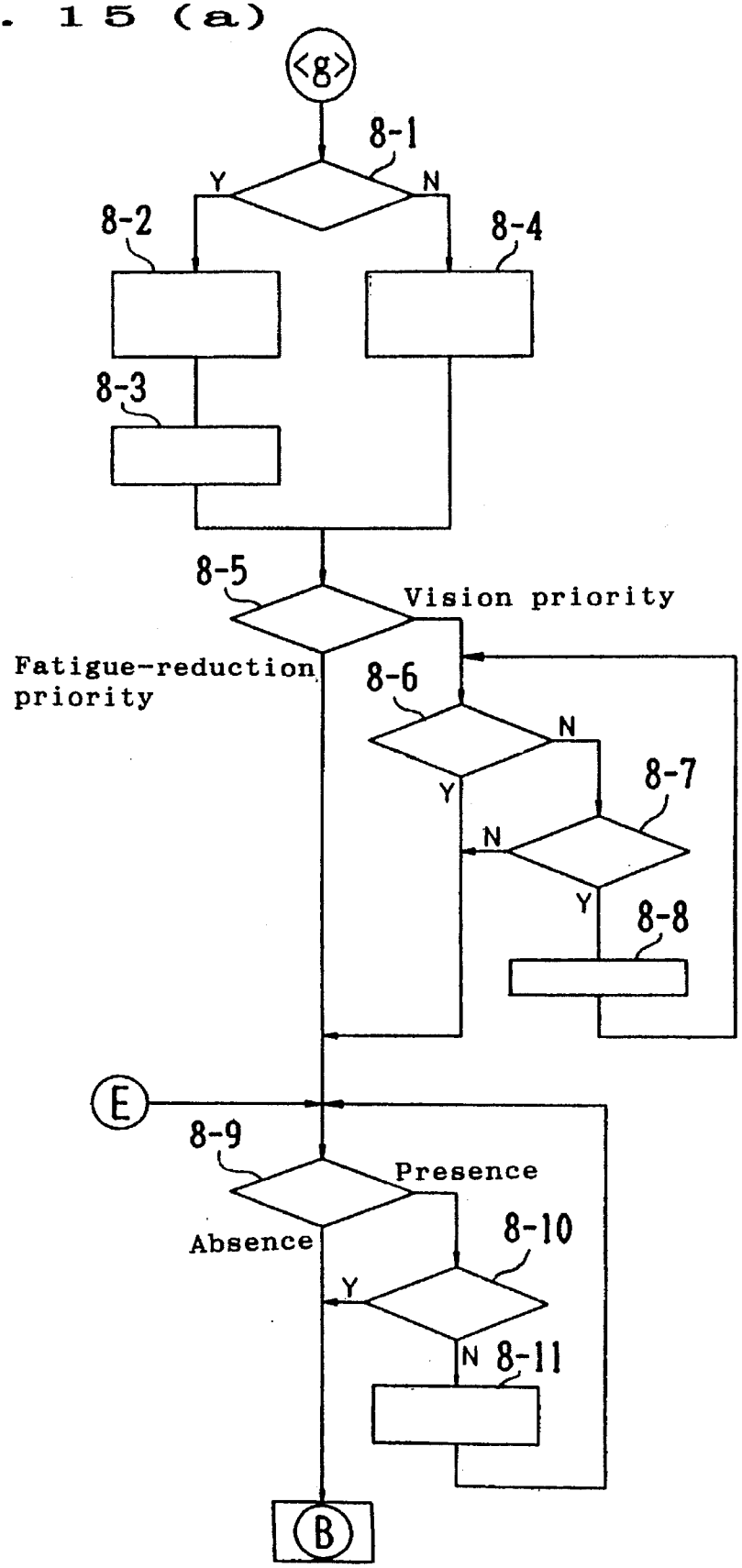
FIGS. 15(a) and 15(b) are flowcharts for describing a routine procedure in the corrected-degrees control program at the time that the anisometropia exists but no astigmatism exists and the hypermetropa exists.

When the anisometropia exists and the astigmatism-free farsightedness exists, the control circuit 50 judges as shown in FIGS. 15(*a,b*) whether an initial spectacles wear is made (Step 8-1). If the answer is found to be YES at Step 8-1, then the degree of a degree-strong eye is set identical to that of a degree-weak eye (Step 8-2) and the degree-strong eye is adjusted to a degree obtained by adding S+0.75 D to the degree-strong eye (Step 8-3). If the answer is found to be NO at Step 8-1, then the degree-weak eye is kept as it is and the degree-strong eye is adjusted to a degree obtained by adding S+0.75 D to a previous spectacle degree (Step 8-4) or to a completely-corrected degree. In accordance with a main appeal of a person to be examined, for judging whether a priority should be given to the vision or a visual fatigue should be lessened (Step 8-5), the examiner performs an easy-to-see confirmation when the priority should be given to the vision (Steps 8-6 through 8-8). After a physical disorder has been confirmed (Steps 8-9 through 8-11), the examiner next proceeds to a binocular visual acuity test step for the eyes regarded as anisometropic, which will be described later.

<h>

Figure 16:
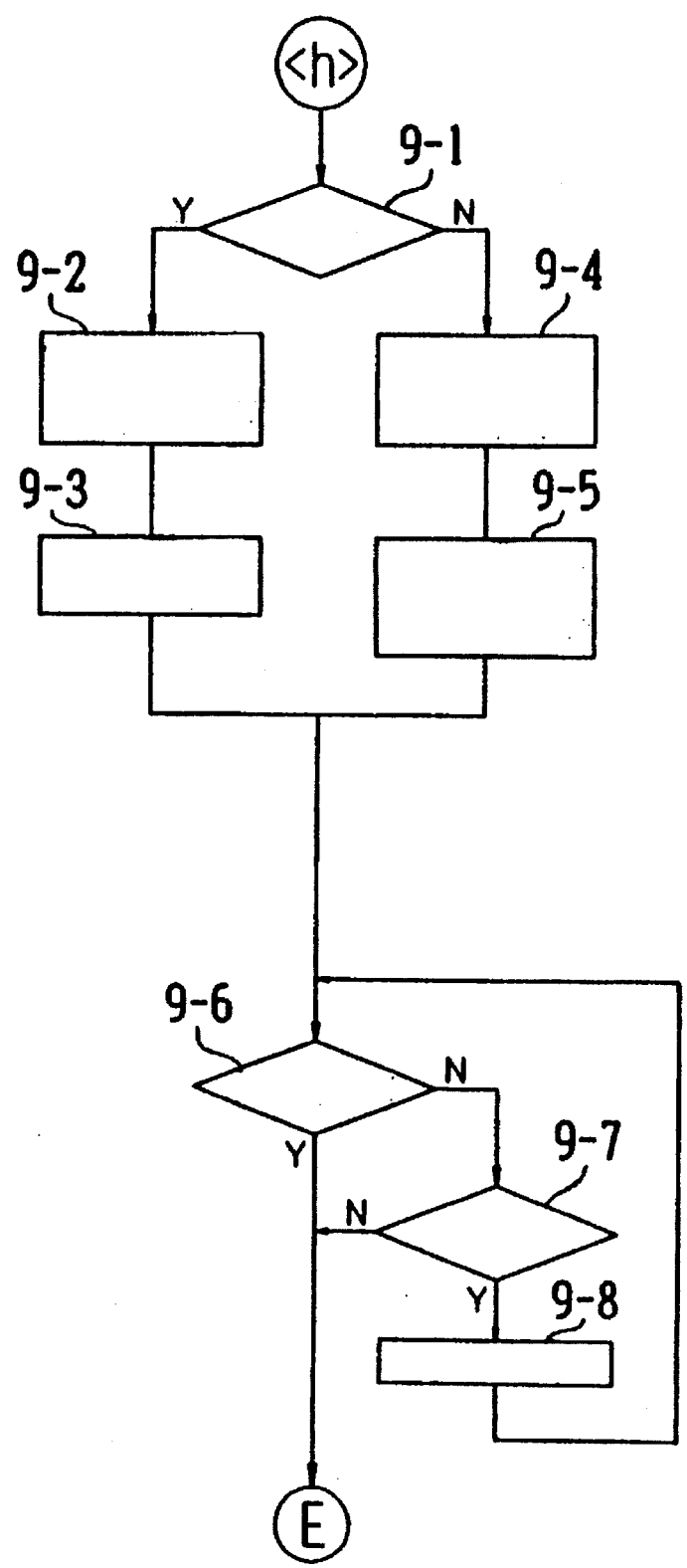
FIGS. 16(a) and 16(b) are flowcharts for describing a routine procedure in the corrected-degrees control program at the time that the anisometropia exists but no astigmatism exists and the near sightedness exists.

When both eyes are regarded as anisometropic and the astigmatism-free near sightedness exists, the control circuit 50 judges as shown in FIGS. 16(*a,b*) whether an initial spectacles wear is made (Step 9-1). If the answer is found to be YES at Step 9-1, then the control circuit 50 performs an arithmetic process (hereinafter called arithmetic process A') for setting both eyes to S1' based on the table A with a degree-weak eye having a spherical degree as reference (Step 9-2) and adds S−0.75 D to a degree-strong eye (Step 9-3) thereby to calculate adjusted degrees. If the answer is found to be NO at Step 9-1, then the control circuit 50 performs an arithmetic process (hereinafter called arithmetic process B') for setting the degree-weak eye having the spherical degree to a degree reduced by ΔS2 based on the table B (Step 9-4). Further, the control circuit 50 adds S−0.75 D to a previous spectacle spherical degree in the case of the degree-strong eye or sets the degree of the degree-strong eye to a completely-corrected degree when it exceeds the completely-corrected degree due to the addition of S−0.75 D to the previous spectacle spherical degree (when the spectacle degree exceeds the completely-corrected degree, it is hereafter set to the completely-corrected degree in the case of a process for adding degrees to the previous spectacles) (Step 9-5). Lenses associated with the degrees obtained by such adjustments are set to the subjective refractive power inspecting device 2. The examiner performs an easy-to-see confirmation (Steps 9-6 through 9-8), followed by proceeding to the confirmation of a physical disorder (i.e., to Step 8-9 referred to above). Thereafter, the examiner advances the optometry to the binocular visual acuity test step for the eyes regarded as anisometropic.

<i>

Figure 17A:
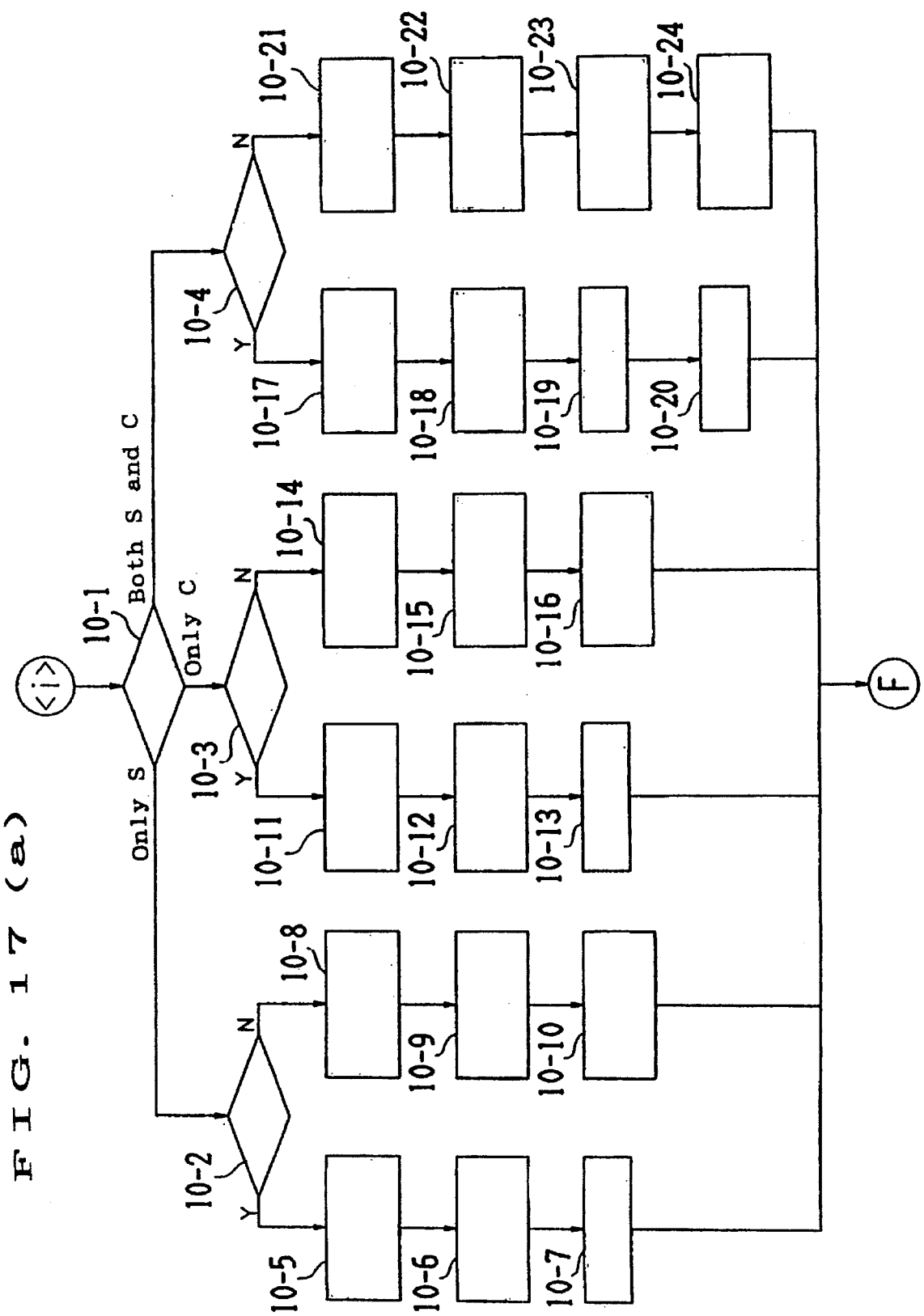

When the farsightedness exists at Step 1-10 (i.e., when both eyes are regarded as anisometropic and the oblique astigmatism-free astigmatism and the farsightedness exist), the control circuit 50 judges as shown in FIGS. 17(*a,b,c*) whether the type of anisometropia belongs to only either a spherical surface or astigmatism or to both sphericity and astigmatism (Step 10-1). Thereafter, the control circuit 50 judges according to the type whether an initial spectacles wear is made (Steps 10-2 through 10-4).

—When the type of anisometropia belongs to the spherical surface alone and the spectacles are initially loaded:

The control circuit 50 performs the arithmetic process C (Step 10-5), carries out a process for adding ΔC1/2 to a binocular spherical degree S to produce an equivalent spherical surface (Step 10-6) and thereafter adds S+0.75 D to a degree-strong eye (Step 10-7) thereby to calculate adjusted degrees.

—When the type of anisometropia belongs to the spherical surface alone and the initial spectacles wear is not performed:

The control circuit 50 performs the arithmetic process D (Step 10-8), executes a process for adding ΔC2/2 to the binocular spherical degree S to produce an equivalent spherical surface (Step 10-9) and thereafter adds S+0.75 D to a previous spectacle degree of a degree-strong eye thereby to calculate adjusted degrees.

—When the type of anisometropia belongs to the astigmatism alone and the initial spectacles wear is performed:

The control circuit 50 performs an arithmetic process (hereinafter called arithmetic process C') for setting astigmatic degrees of both eyes to C1' based on the table C with an astigmatic and degree-weak eye as reference (Step 10-11). Next, the control circuit 50 adds ΔC1/2 to the binocular spherical degree S to produce an equivalent spherical surface (Step 10-12). Thereafter, the control circuit 50 adds C−0.75 D to an astigmatic and degree-strong eye (Step 10-13) thereby to calculate adjusted degrees.

—When the type of anisometropia belongs to the astigmatism alone and the initial spectacles wear is not performed:

The control circuit 50 performs an arithmetic process (hereinafter called arithmetic process D') for setting each astigmatic and degree-weak eye to an astigmatic degree reduced by ΔC2 based on the table D (Step 10-14). Next, the control circuit 50 adds ΔC2/2 to the binocular spherical degree S to produce an equivalent spherical surface (Step 10-15) and thereafter adds C−0.75 D to a previous spectacle degree of the astigmatic and degree-strong eye (Step 10-16) thereby to calculate adjusted degrees.

—When the type of anisometropia belongs to both the spherical surface and the astigmatism and the initial spectacles wear is performed:

The control circuit 50 performs the same process as that at Steps 10-11 through 10-13 (Steps 10-17 through 10-19) and thereafter adds S+0.75 D to a spherical and degree-strong eye (Step 10-20) thereby to calculate adjusted degrees.

—When the type of anisometropia belongs to both the spherical surface and the astigmatism and the spectacles are not initially loaded:

The control circuit 50 executes the same process as that at Steps 10-14 through 10-16 referred to above (Steps 10-21 through 10-23) and thereafter adds S+0.75 D to a previous spectacle degree of the spherical and degree-strong eye (Step 10-24) thereby to calculate adjusted degrees.

Figure 18A:
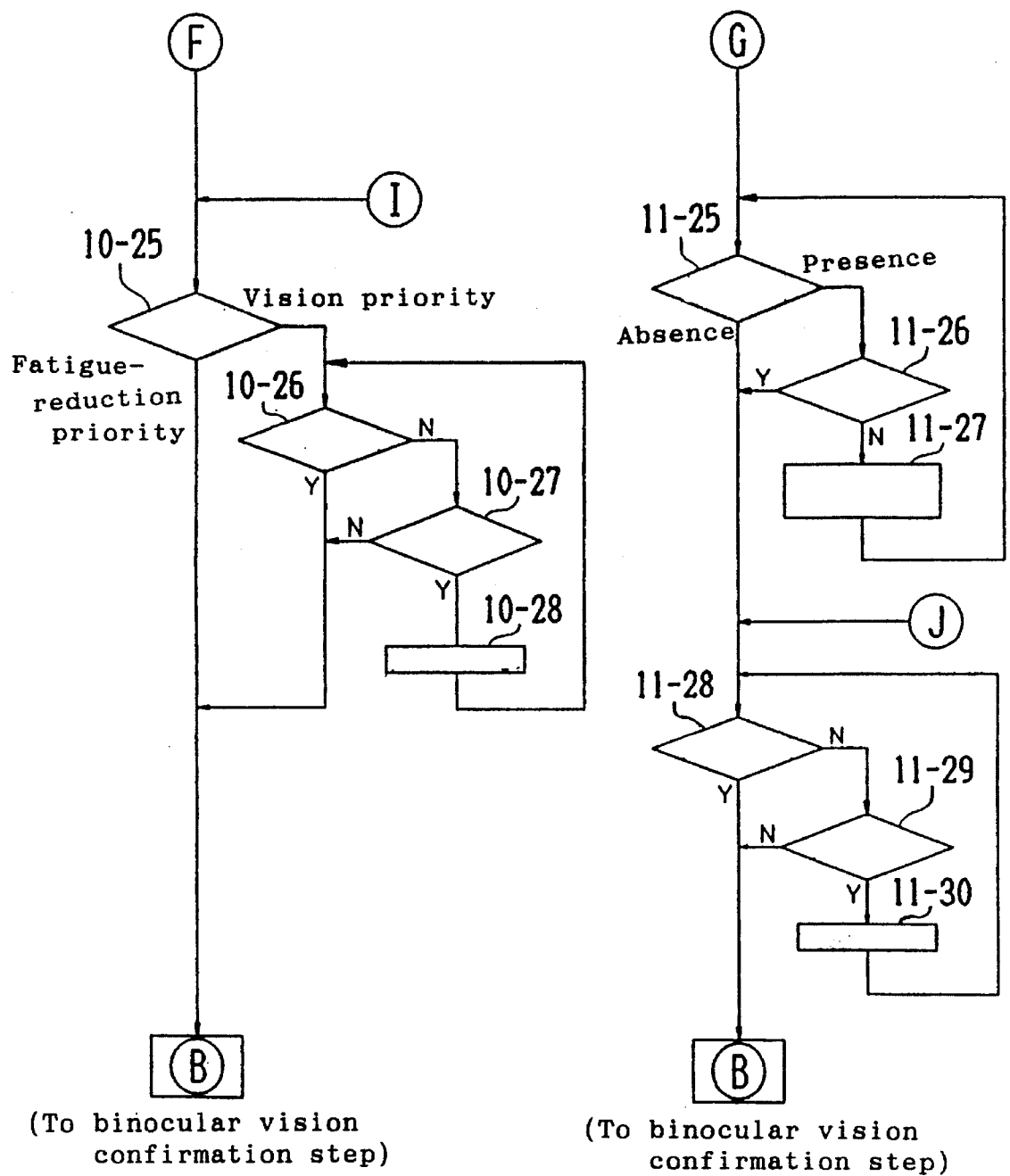

After the adjusted degrees have been calculated by the control circuit 50 in accordance with the paragraphs of—through—, the examiner performs a confirmation based on the same main appeal as that at Steps 8-5 through 8-8 referred to above as shown in FIGS. 18(*a,b*) (Steps 10-25 through 10-28) and advances the optometry to the binocular visual acuity test step for the eyes treated as anisometropic.

<j>

Figure 19A:
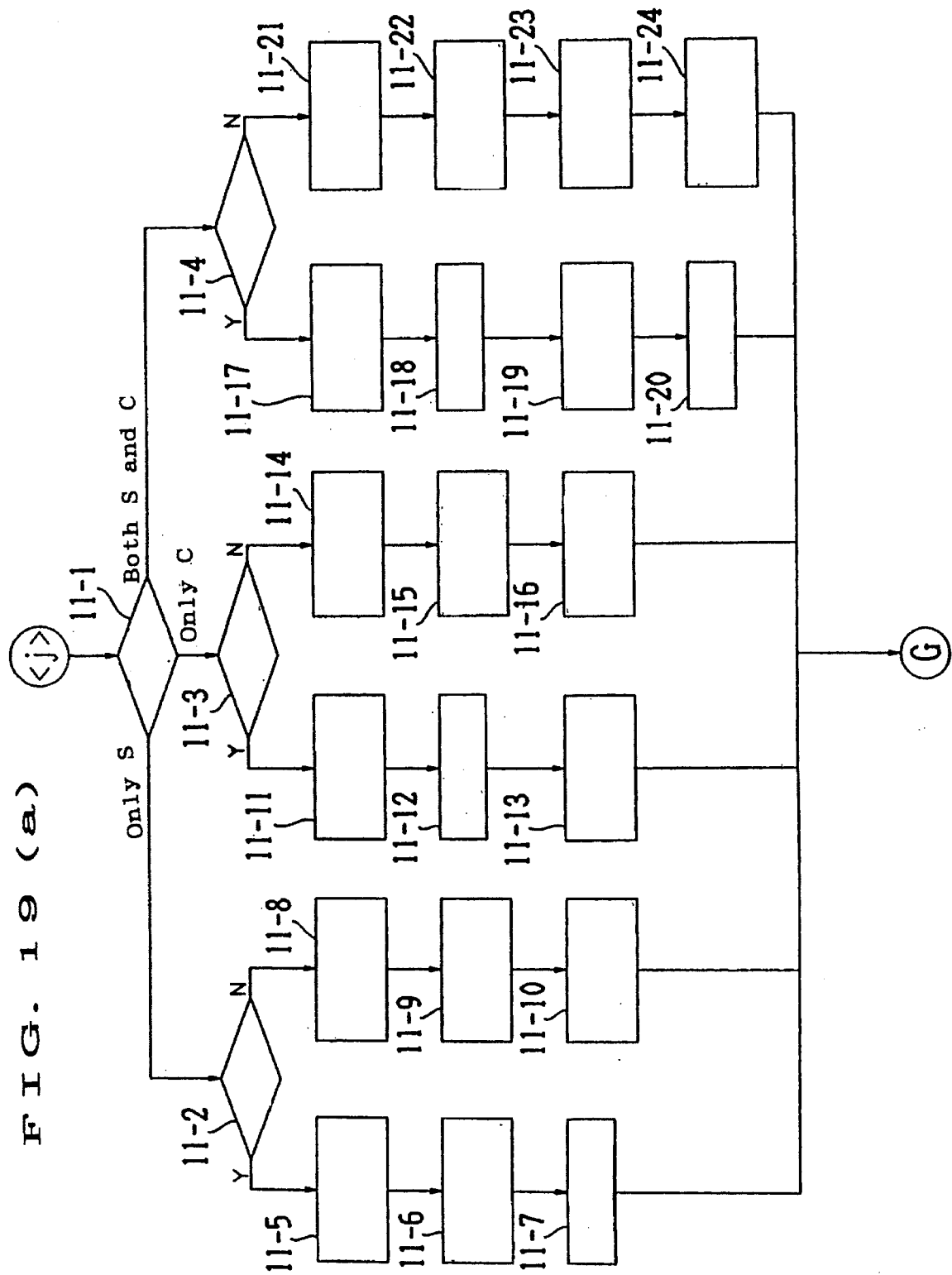

When the near sightedness exists at Step 1-10 (i.e., when the eyes are anisometropic and the oblique astigmatism-free astigmatism and the nearsightedness exist), the control circuit 50 judges as shown in FIGS. 19(*a,b,c*) whether the type of anisometropia belongs to only either a spherical surface or astigmatism or to both the spherical surface and the astigmatism (Step 11-1) in the same manner as the aforementioned <i>. Thereafter, the control circuit 50 judges according to the type whether the spectacles are initially loaded (Steps 11-2 through 11-4) and performs the following processes.

—When the type of anisometropia belongs to the spherical surface alone and the initial spectacles wear is made:

The control circuit 50 executes the arithmetic processes C and A' and thereafter adds S−0.75 D to each spherical and degree-strong eye thereby to calculate adjusted degrees (Steps 11-5 through 11-7).

—When the type of anisometropia belongs to the spherical surface alone and the initial spectacles wear is not performed:

The control circuit 50 executes the arithmetic process D and the arithmetic process B' and thereafter adds S−0.75 D to the spherical and degree-strong eye thereby to calculate adjusted degrees (Steps 11-8 through 11-10).

—When the type of anisometropia belongs to the astigmatism alone and the initial spectacles wear is performed:

The control circuit 50 executes the arithmetic process C' and thereafter adds C−0.75 D to an astigmatic and degree-strong eye. Subsequently, the control circuit 50 executes the arithmetic process A to calculate adjusted degrees (Steps 11-11 through 11-13).

—When the type of anisometropia belongs to the astigmatism alone and the initial spectacles wear is not performed:

The control circuit 50 executes the arithmetic process D' and thereafter adds C−0.75 D to a previous spectacle degree of the astigmatic and degree-strong eye, followed by execution of the arithmetic process B, thereby calculating adjusted degrees (Steps 11-14 through 11-16).

—When the type of anisometropia belongs to both the spherical surface and the astigmatism and the initial spectacles wear is made:

The control circuit 50 executes the arithmetic process C', a process for adding C−0.75 D to the astigmatic and degree-strong eye, the arithmetic process A' and a process for adding S−0.75 D to the spherical and degree-strong eye thereby to calculate adjusted degrees (Steps 11-17 through 11-20).

—When the type of anisometropia belongs to both the spherical surface and the astigmatism and the initial spectacles wear is not performed:

The control circuit 50 executes the arithmetic process D', a process for adding C−0.75 D to the previous spectacle degree of the astigmatic and degree-strong eye, the arithmetic process B' and a process for adding S−0.75 D to a previous spectacle degree of the spherical and degree-strong eye thereby to calculate adjusted degrees (Steps 11-21 through 11-24).

After the adjusted degrees have been calculated by the control circuit 50 in accordance with the paragraphs of—through—, the examiner proceeds to the confirmation step. Since all the spherical degrees are adjusted under the process of <j>, the examiner firstly performs a physical disorder confirmation similar to that at Steps 8-9 through 8-11 referred to above as shown in FIGS. 18(*a,b,c*) (Steps 11-25 through 11-27). Thereafter, the examiner performs an easy-to-see confirmation similar to that at Steps 3-4 through 3-6 (Steps 11-28 through 11-30).

\<k\>

Figure 20:
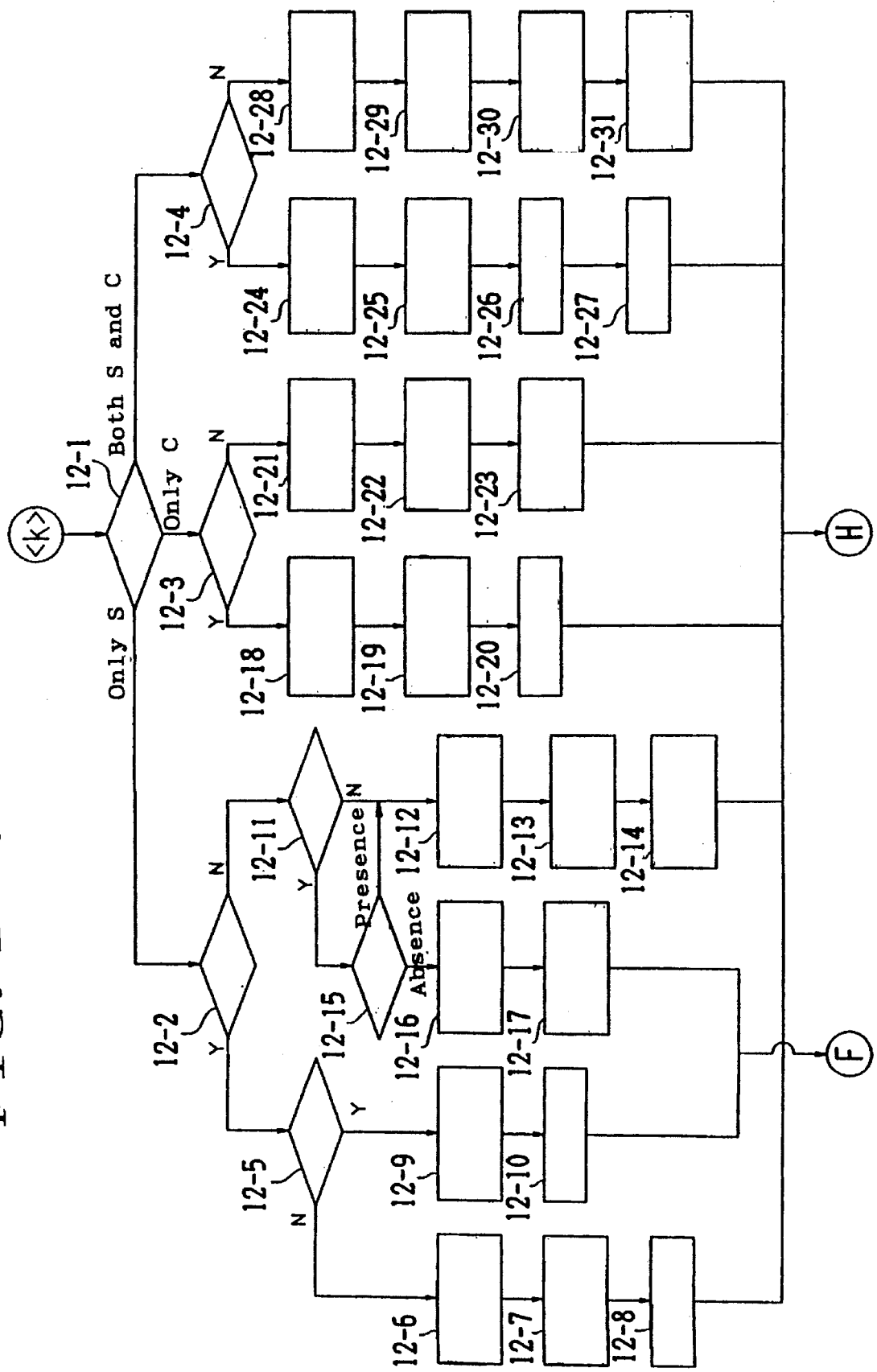

When the farsightedness exists at Step 1-11 (i.e., when both eyes are anisometropic and the oblique astigmatism and the farsightedness exist), the control circuit 50 judges in the same manner as the aforementioned \<i\> as shown in FIGS. 20(a,b,c) whether the type of anisometropia belongs to only either a spherical surface or astigmatism or to both the spherical surface and astigmatism (Step 12-1). Thereafter, the control circuit 50 judges according to the type whether an initial spectacles wear is made (Steps 12-2 through 12-4).

—When the type of anisometropia belongs to the spherical surface alone and the spectacles are initially loaded:

The control circuit 50 judges whether an astigmatic degree C is less than or equal to −0.5 D (Step 12-5). If the astigmatic degree C is found to exceed −0.5 D, then the control circuit 50 judges, as adjusted degrees, degrees obtained by executing the arithmetic process C, an equivalent spherical process for adding C/2 to a binocular spherical degree S and a process for adding S+0.75 D to a spherical and degree-strong eye (Steps 12-6 through 12-8). If the astigmatic degree C is found to be less than or equal to −0.5 D, then the control circuit 50 judges the astigmatism as negligible and hence sets the astigmatic degree C to 0. Further, the control circuit 50 performs a process for adding half the astigmatic degree C to the spherical degree S [when the astigmatic degree C is 0.25 D, the equivalent spherical process is not executed] (Step 12-9) and a process for adding S+0.75 D to the spherical and degree-strong eye (Step 12-10) thereby to calculate adjusted degrees.

—When the type of anisometropia belongs to the spherical surface alone and the initial spectacles wear is not made:

The control circuit 50 judges whether the astigmatic degree C is less than or equal to −0.5 D (Step 12-11). If the astigmatic degree C is found to exceed −0.5 D, then the control circuit 50 executes the arithmetic process D, an equivalent spherical process for adding $\Delta C2/2$ to the binocular spherical degree S and a process for adding S+0.75 D to a previous spectacle degree of the spherical and degree-strong eye (Steps 12-12 through 12-14) thereby to calculate adjusted degrees.

If the astigmatic degree C is found to be less than or equal to −0.5 D, then the control circuit 50 judges whether the astigmatism exists in the previous spectacles (Step 12-15). If the astigmatism is found not to exist in the previous spectacles, then the control circuit 50 judges the astigmatism as negligible and sets the astigmatic degree C to 0. Further, the control circuit 50 executes a process for adding half the astigmatic degree C to the spherical degree S (Step 12-16) and a process for adding S+0.75 D to the previous spectacle degree of the spherical and degree-strong eye (Step 12-17) thereby to calculate adjusted degrees. If the astigmatism is found to exist in the previous spectacles, then the control circuit 50 executes Steps 12-12 through 12-14 referred to above to calculate adjusted degrees.

—When the type of anisometropia belongs to the astigmatism alone and the initial spectacles wear is made:

The control circuit 50 executes a process similar to the paragraph—in the aforementioned \<i\> thereby to calculate adjusted degrees (Steps 12-18 through 12-20).

—When the type of anisometropia belongs to the astigmatism alone and the initial spectacles wear is not made:

The control circuit 50 executes a process similar to the paragraph—in the aforementioned \<i\> thereby to calculate adjusts degrees (Steps 12-21 through 12-23).

—When the type of anisometropia belongs to both the spherical surface and the astigmatism and the initial spectacles wear is made:

The control circuit 50 executes a process similar to the paragraph—in the aforementioned \<i\> thereby to calculate adjusted degrees (Steps 12-24 through 12-27).

—When the type of anisometropia belongs to both the spherical surface and the astigmatism and the initial spectacles wear is not made:

The control circuit 50 executes a process similar to the paragraph—in the aforementioned \<i\> thereby to calculate adjusted degrees (Steps 12-28 through 12-31).

Figure 22:
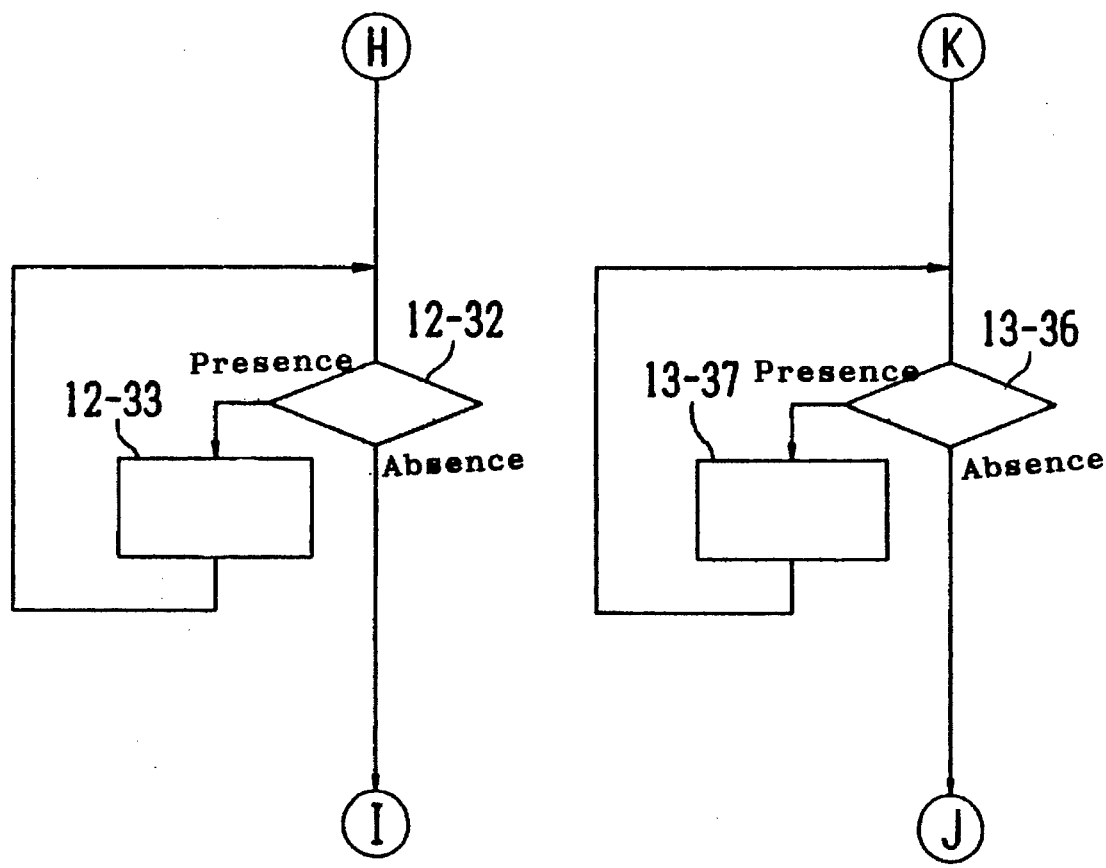
FIGS. 22(a) and 22(b) are flowcharts for describing a malaise selection mode of the corrected-degrees control program where the anisometropia and the oblique astigmatism (both the hypermetropa and the near sightedness) exist.

In the case of Steps 12-10 and 12-17 in which the spherical degree has been set to 0 as negligible, the examiner proceeds to Step 10-25 for confirming whether the priority should be given to the vision or the visual fatigue should be lessened, without confirming the eye physical disorder. Since the astigmatic degree is adjusted except when Step 10-25 referred to above is executed, the examiner performs a physical disorder confirmation similar to that at Steps 7-8 and 7-9 (Steps 12-32 and 12-33) as shown in FIGS. 22(a,b), followed by proceeding to Step 10-25 referred to above.

Thereafter, the examiner advances the optometry to the binocular visual acuity confirmation step for the eyes regarded as anisometropic.

\<l\>

Figure 21:
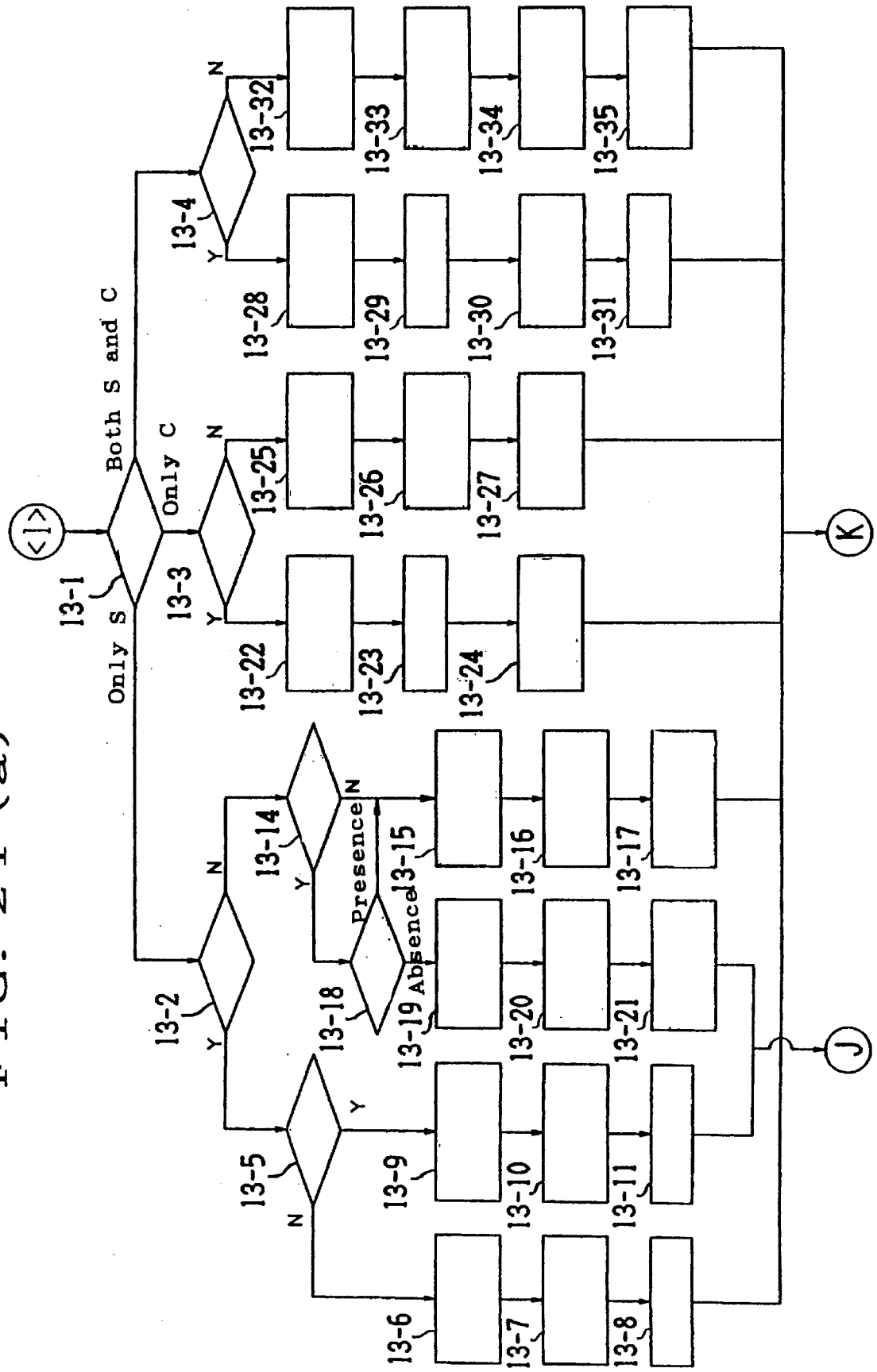
FIGS. 21(a)–21(c) are flowcharts for describing a routine procedure in the corrected-degrees control program at the time that the anisometropia and the oblique astigmatism exist and the near sightedness exists.

When the near sightedness exists at Step 1-11 (when both eyes are regarded as anisometropic and the oblique astigmatism and the near sightedness exist), the control circuit 50 judges in the same manner as the aforementioned \<i\> as shown in FIGS. 21(a,b,c) whether the type of anisometropia belongs to only either a spherical surface or astigmatism or to both the spherical surface and the astigmatism (Step 13-1). Thereafter, the control circuit 50 judges according to the type whether an initial spectacles wear is made (Steps 13-2 through 13-4) and executes the next processing.

—When the type of anisometropia belongs to the spherical surface alone and the spectacles are initially loaded:

The control circuit 50 judges whether an astigmatic degree C is less than or equal to −0.5 D (Step 13-5). When the astigmatic degree C exceeds −0.5 D, the control circuit 50 executes a process similar to the paragraph—in the aforementioned \<j\> thereby to calculate adjusted degrees (Steps 13-6 through 13-8). If the astigmatic degree C is found to be less than or equal to −0.5 D, then the control circuit 50 judges the astigmatism as negligible and hence sets the astigmatic degree C to 0 (Step 13-9). Further, the control circuit 50 executes the arithmetic process A' (Step 13-10) and a process for adding S−0.75 D to a spherical and degree-strong eye (Step 13-11) thereby to calculate adjusted degrees.

—When the type of anisometropia belongs to the spherical surface alone and the initial spectacles wear is not made:

The control circuit 50 determines whether the astigmatic degree C is less than or equal to −0.5 D (Step 13-14). When the astigmatic degree C exceeds −0.5 D, the control circuit 50 executes a process similar to the paragraph—in the aforementioned \<j\> to calculate adjusted degrees (Steps 13-15 through 13-17). When the astigmatic degree C is less than or equal to −0.5 D, the control circuit 50 first judges whether the astigmatism exists in the previous spectacles (Step 13-18). Next, when no astigmatism exists in the previous spectacles, the control circuit 50 judges the astigmatism as negligible and hence sets the astigmatic degree to 0 (Step 13-19). Further, the control circuit 50 executes the arithmetic process B' (Step 13-20) and a process for adding S−0.75 D to a previous spectacle degree of a spherical and degree-strong eye (Step 13-21) thereby to calculate adjusted degrees. When the astigmatism exists in the previous spectacles, the control circuit 50 executes the same process as that at Steps 13-15 through 13-17 referred to above to calculate adjusted degrees.

—When the type of anisometropia belongs to the astigmatism alone and the initial spectacles wear is made:

The control circuit 50 executes a process similar to the paragraph—in the aforementioned <j> thereby to calculate adjusted degrees (Steps 13-22 through 13-24).

—When the type of anisometropia belongs to the astigmatism alone and the initial spectacles wear is not performed:

The control circuit 50 executes a process similar to the paragraph—in the aforementioned <j> thereby to calculate adjusted degrees (Steps 13-25 through 13-27).

—When the type of anisometropia belongs to both the spherical surface and the astigmatism and the initial spectacles wear is made:

The control circuit 50 executes a process similar to the paragraph—in the aforementioned <j> thereby to calculate adjusted degrees (Steps 13-28 through 13-31).

—When the type of anisometropia belongs to both the spherical surface and the astigmatism and the initial spectacles wear is not made:

The control circuit 50 executes a process similar to the paragraph—in the aforementioned <j> thereby to calculate adjusted degrees (Steps 13-32 through 13-35).

Since the spherical degree is set to 0 as negligible in the process of proceeding to Steps 13-11 and 13-21 referred to above, the examiner performs the easy-to-see confirmation at Step 11-28 referred to above without confirming the physical disorder and advances the optometry to the next binocular visual acuity confirmation step for the eyes regarded as anisometropic. Since the astigmatic degree is adjusted in other flow, the examiner executes steps 13-36 and 13-37 for confirmation of the physical disorder as shown in FIGS. 22(*a,b*) and proceeds to the easy-to-see confirmation step 11-28.

Thereafter, the examiner proceeds to the visual acuity confirmation step for the eyes regarded as anisometropic.

(3) After the completely reformed values have been corrected in accordance with the processes of <a> through <l>, the program feed switch is depressed to successively execute the confirmation for the binocular visual acuity, the determination for prescribed values used for far sight and a degree adjusting process for presbyopia.
Subsequent to processes of <a> through <f>

Figure 23A:
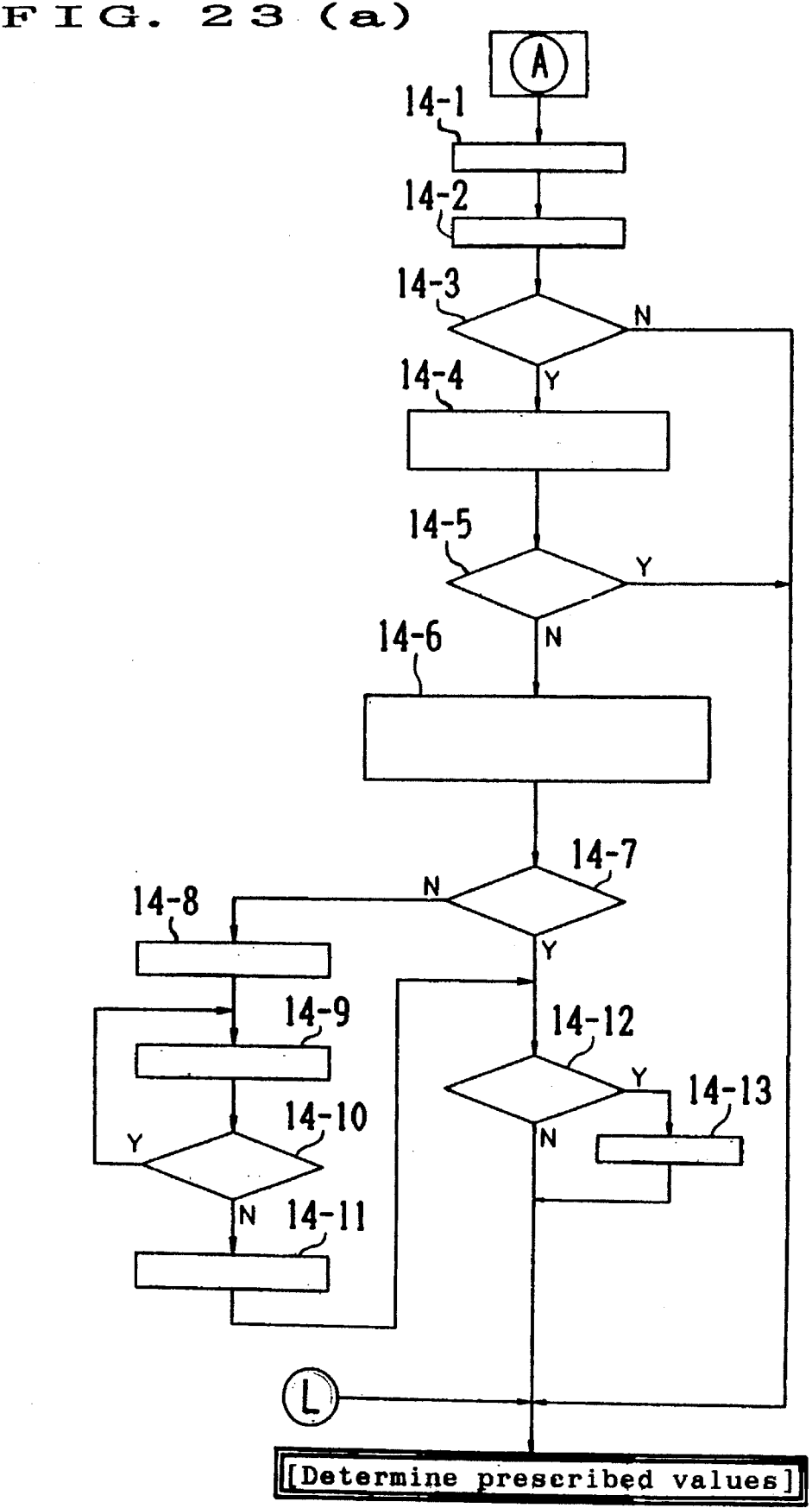

In response to a signal from the program feed switch, the control circuit 50 sends a signal indicative of a Landolt ring object to the object indicating device 3. As shown in FIGS. 23(*a,b*), the control circuit 50 confirms binocular vision in accordance with the indicated Landolt ring object (Step 14-1). If the eyes are not extraordinary, then the program feed switch is depressed to determine prescribed values for far sight (Step 14-2).

Next, the control circuit 50 judges whether the degrees should be adjusted due to the presbyopia (Step 14-3). If the presbyopia is found to exist, then the eyes are regarded as presbyopic if over 35 years, for example, and the control circuit 50 makes a decision about it based on input data about age of case history data. If the eyes are found not to be regarded as presbyopic based on the presbyopia decision, then the prescribed values for far sight are determined as prescribed values used for a person to be examined.

If the eyes are judged as presbyopic, then lenses corresponding to binocular completely-corrected degrees are set to the subjective refractive power inspecting device again. Optical axis of subjective refracting power inspecting device converges where the crossing point is near about 35 cm deistance and instructions for measuring additive degrees for near sight are displayed on a display monitor. The controller enters into an ADD additive degree mode and can operate the input switch group 18 to add spherical degrees. The examiner presents a cross-grid type object for near sight and measures additive degrees for the eyes (Step 14-4). Further, the examiner depresses the program feed switch to input the measured degrees to be added.

If the additive degree is 0, then the control circuit 50 determines prescribed values for far sight as prescribed values for the person to be examined as they are (Step 14-5). The control circuit 50 converts a difference between each of the binocular completely-corrected values and each of the spherical degrees adjusted by the calculation of the prescribed values for far sight and an astigmatism equivalent spherical difference into additive degrees and regards those obtained by subtracting these from the measured degrees to be added, as degrees for near sight (Step 14-6). Thereafter, the examiner confirms whether the visual acuity is greater than or equal to 0.7 (Step 14-7). If the answer is found to be NO at Step 14-7, then the examiner confirms the visual acuity (Step 14-8). Further, the examiner adds S+0.25 D to the eyes (Step 14-9) and confirms whether the visual acuity is brought into UP (Step 14-10). If the answer is found to be YES at Step 14-10, then S+0.25 D is added to both eyes (Step 14-9). If the visual acuity is found to remain unchanged or fall, then S−0.25 D is added to both eyes to return the degrees to the original state (Step 14-11).

Subsequently, the examiner depresses the program feed switch after having confirmed the visual acuity and proceeds to the next step. The control circuit 50 judges whether a person to be examined initially puts on his/her spectacles (Step 14-12). If the answer is found to be YES at Step 14-12, then the control circuit 50 adds a spherical S−0.25 D to both eyes to adjust the degrees (Step 14-13) and judges the adjusted values as prescribed values for the person.
Subsequent to processes of <g> through <l>

Figure 24:
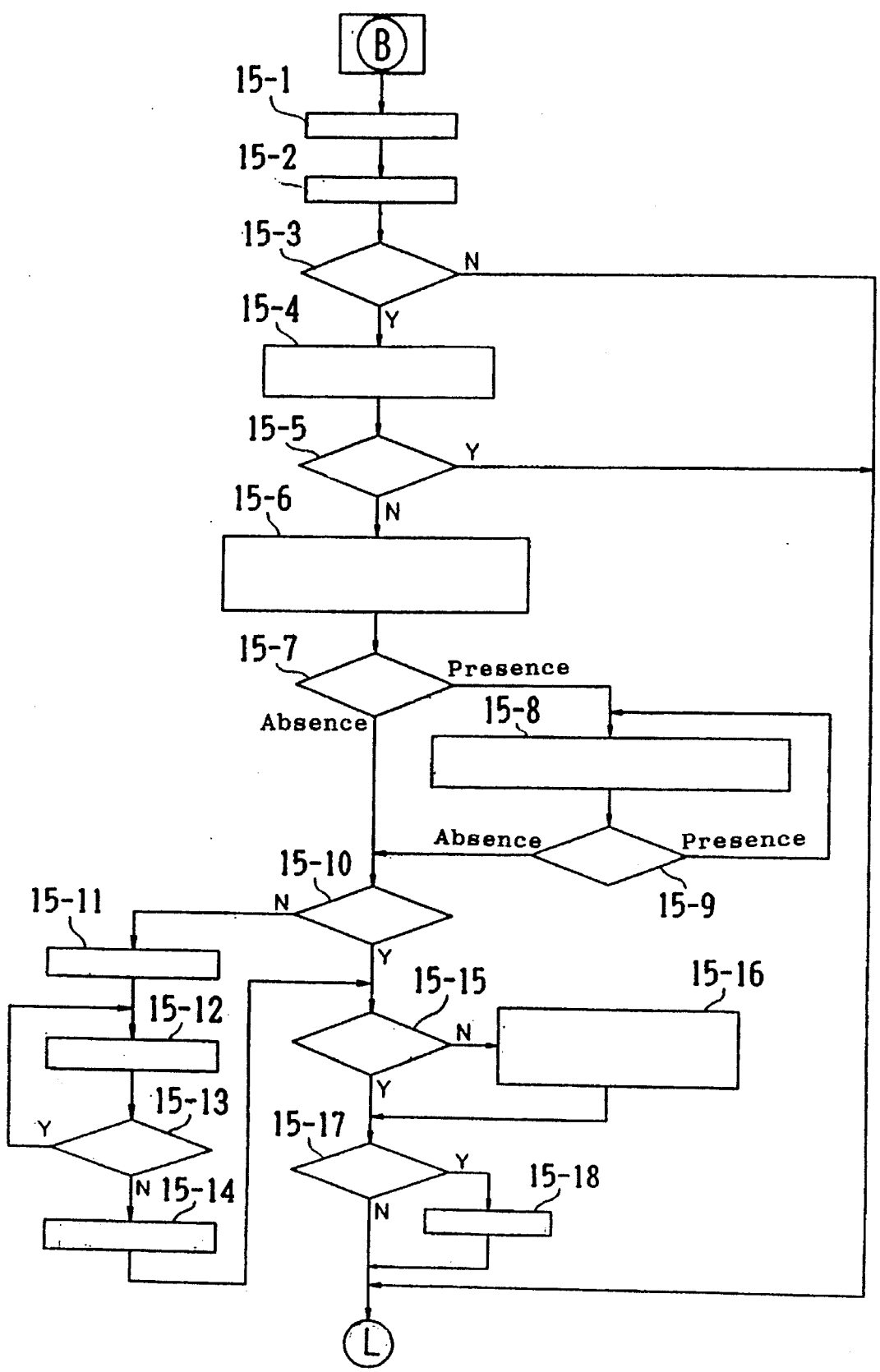
FIGS. 24(a) and 24(b) are flowcharts for describing a routine procedure for determining prescribed values, of the corrected-degrees control program where the anisometropia exists.

As shown in FIG. 24, the examiner confirms binocular visual acuity (Step 15-1) and determines prescribed values for far sight (Step 15-2). Thereafter, the control circuit 50 judges whether the eyes are presbyopic (Step 15-3).

If the answer is YES at Step 15-3, then instructions for measuring an additive degree for near sight on a monocular basis, are displayed on the display monitor. Lenses corresponding to binocular completely-corrected degrees are set to the subjective refractive power inspecting device again. The examiner presents a cross-grid type object for near sight and measures an additive degree on a monocular basis (Step 15-4). Further, the examiner depresses the program feed switch to input each measured degree to be added.

If the additive degree is 0, then the control circuit 50 determines prescribed values for far sight as prescribed values for the person to be examined as they are (Step 15-5). If the additive degree is not 0, then the control circuit 50 adjusts degrees for near sight in a manner similar to Step 14-6 referred to above (Step 15-6). Instructions for confirming a eye physical disorder are displayed on the display monitor and hence the examiner confirms the physical disorder (Step 15-7). If the physical disorder is found to exist at Step 15-7, then an additive degree for a degree-weak eye having a spherical degree for far sight is held as it is and other eye is allowed to approach a degree for the degree-weak eye (Step 15-8). Since the control circuit 50 judges at Step 15-8 whether the degree-weak eye exists, the examiner may simply activate a degree changeover switch. Further, the examiner confirms the physical disorder again (Step 15-9).

If the physical disorder is found not to exist at Step 15-7 or Step 15-9, then the examiner confirms whether the visual acuity is greater than or equal to 0.7 (Step 15-10). If the answer is found to be NO at Step 15-10, then the same adjustment as at Steps 14-8 through 14-11 is executed (Steps 15-11 through 15-14). Further, the examiner depresses the program feed switch and then proceeds to the next step.

The control circuit 50 determines whether the difference in additive degree between the left and right eyes is less than or equal to 0.25 D (Step 15-15). If the answer is found to be NO at Step 15-15, then instructions indicative of the fact that a progressive multifocal lens is not available and a monofocal lens or a bifocal lens is available, are displayed on the display monitor (Step 15-16). It is thereafter judged whether the initial spectacles wear is made (Step 15-17). If the answer is found to be YES at Step 15-17, then a spherical surface S−0.25 D is added to both eyes to adjust the degrees (Step 15-18) and the adjusted degrees are determined as prescribed values for the person to be examined.

Based on the prescribed values determined in the above-described manner, the examiner confirms the feeling of spectacles loading by a centering inspection and determines the final prescribed values.

Any of the values (such as the reduced degrees ΔS1, ΔS2, ΔC1, ΔC2, etc. in the prescribed degree control table lists shown in FIGS. 8 and 9) for calculating the degrees to be prescribed, which are employed in the above embodiment, is a mere example for adjustment reference. It is needless to say that restrictions are not imposed on these values. The values regarded as the anisometropia upon adjustment of the degrees to be prescribed, the value (0.75 D in the present embodiment) of the degree for anisometropia adjustment, etc. make it possible to calculate prescribed degrees that meet an examiner's policy in consideration of conditions or the like of an examined person by providing a function for changing input settings by the controller 4 in advance.

Figure 25A:
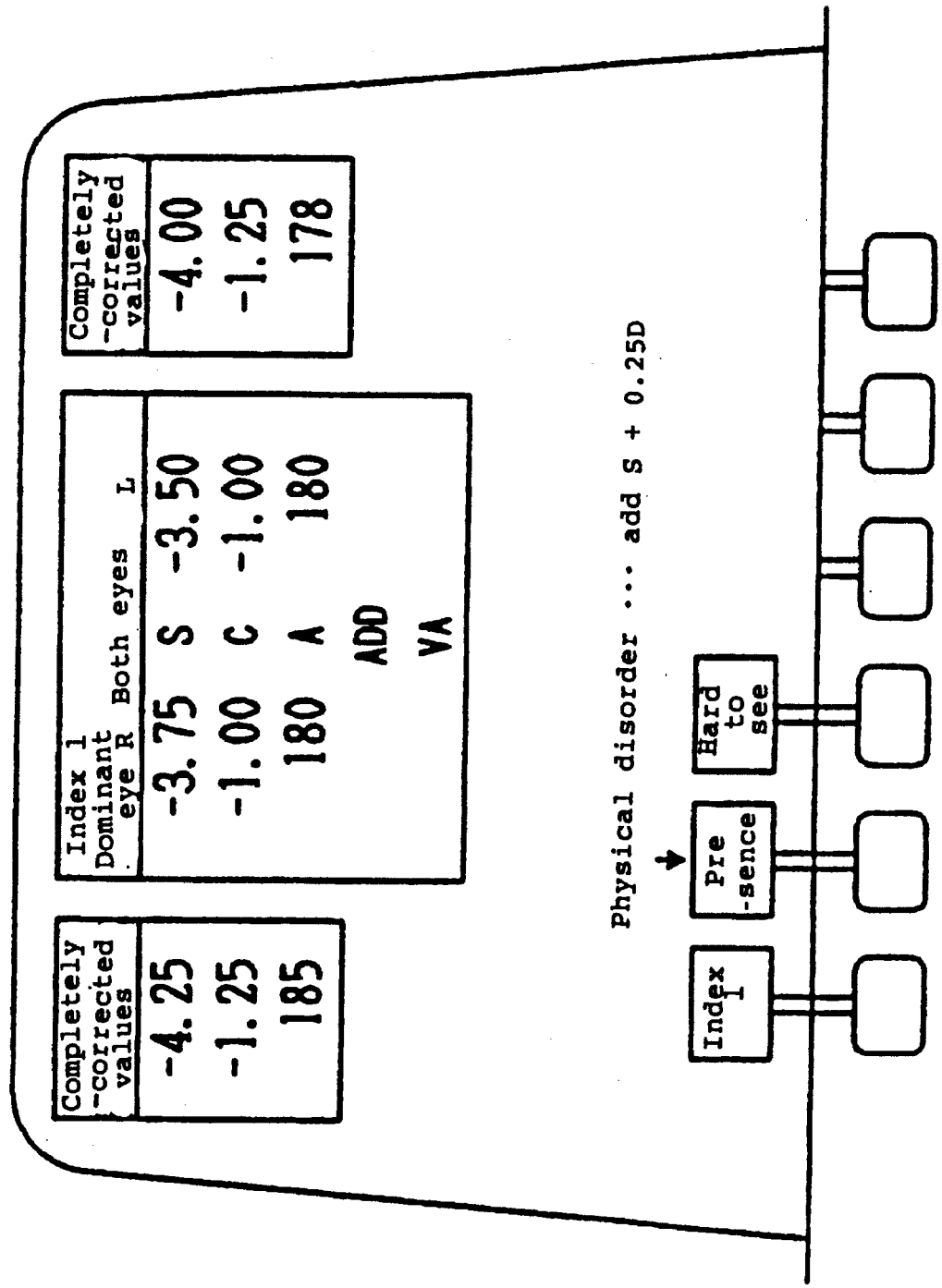
FIGS. 25(a) and 25(b) are views illustrating examples of displays on the screens on which directions to adjust spectacle degrees are indicated.
Figure 25B:
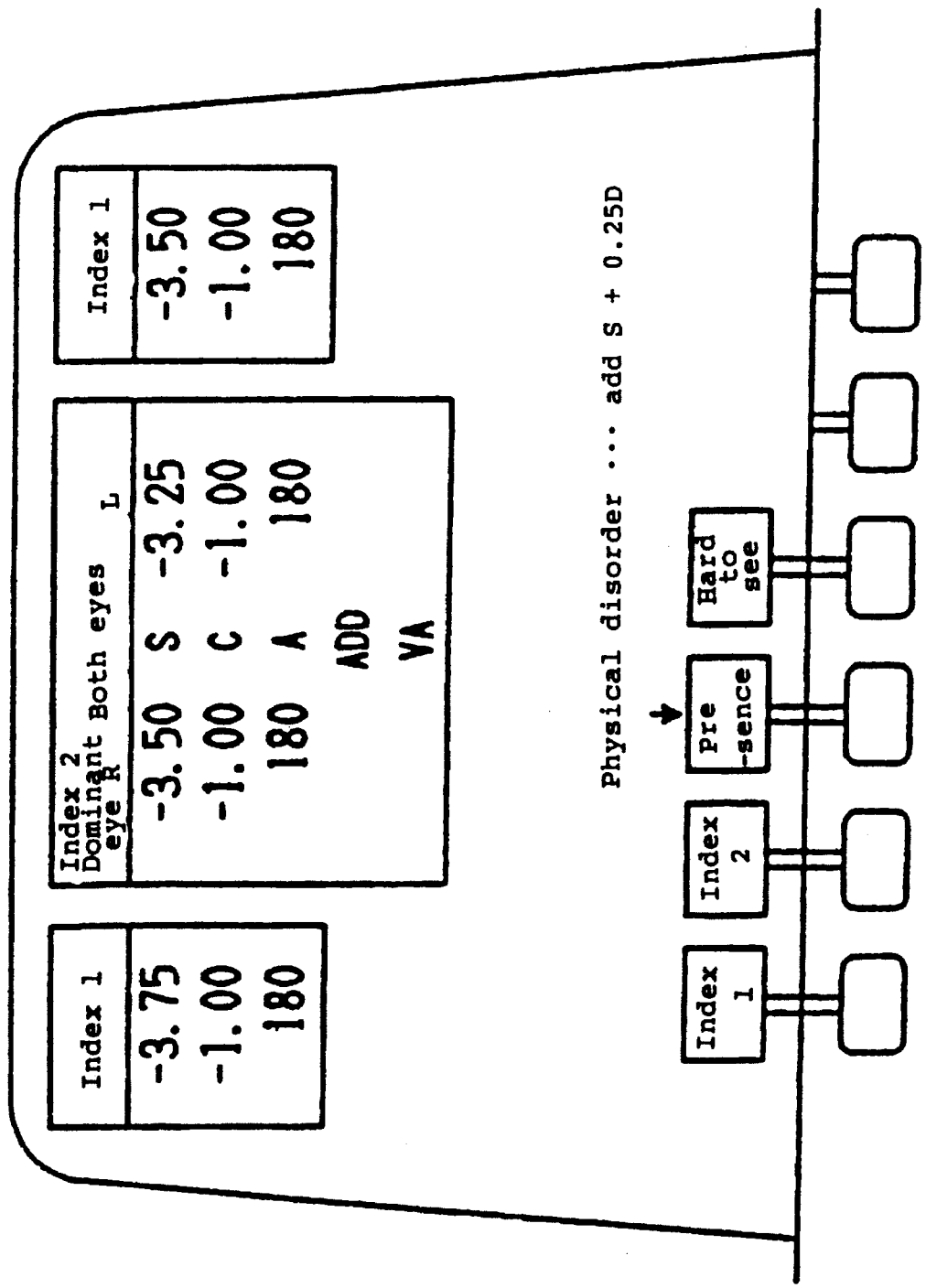

In the above embodiment as well, when it is desired to confirm the easiness-to-see and the physical-disorder, an improvement in operability can be made if the directions for its adjustment are displayed on the display. When the screen-correspondence switch 30 for the "presence" of a physical disorder is depressed where the physical disorder occurs in adjusted degrees (index 1) calculated by the apparatus as shown in FIG. 25(*a*), for example, the next adjusted degrees (index 2) are displayed on the display as shown in FIG. 25(*b*). The examiner can immediately make switching between the index 1 and the index 2 by simply depressing the screen-correspondence switches for the "index 1" and the "index 2."

According to the present invention as described above, many changes and modifications can be made. These are included in the present invention within the scope in which technical ideas are identified.

What is claimed is:

1. An ophthalmic apparatus for obtaining a refractive corrected-degree based on a refractive power of each of eyes to be examined, the ophthalmic apparatus comprising:

refractive power inspecting means for inspecting the refractive power of said each eye;

program storing means for storing therein a program for measuring completely-corrected degrees of said eyes, adjusting the completely-corrected degrees according to factors for adjusting degrees to be corrected and thereby predicting degrees to be prescribed;

input means for inputting data about the factors for adjusting the degrees to be corrected;

program conducting means for advancing the program stored in said program storing means;

control means for sequentially activating said ophthalmic apparatus in accordance with the program and processing the result of inspection by completely-corrected degree inspecting means and the data input by said input means thereby to predict prescribed degrees; and display means for displaying the prescribed degrees predicted by said control means.

2. An ophthalmic apparatus according to claim 1, wherein said control means includes storing means for storing therein quantities of correction based on degrees of near sightedness and astigmatism.

3. An ophthalmic apparatus according to claim 1, wherein said control means stores therein correction quantities varied according to the presence or absence of the history of use of a refraction correcting device and the data input by said input means shows the presence or absence of the refraction correcting device.

4. An ophthalmic apparatus according to claim 1, wherein said program has different correcting procedures each including at least one of the presence or absence of anisometropia, astigmatism and oblique astigmatism and either far sightedness or near sightedness as an element.

5. An ophthalmic apparatus according to claim 1, further including display means for describing operational procedures of an examiner, which displays procedures necessary for respective steps pursuant to the program.

6. An ophthalmic apparatus for obtaining a refractive corrected-degree based on a refractive power of each of eyes to be examined, said ophthalmic apparatus comprising:

a subjective refractive power inspecting device for inspecting a subjective refractive power of said each eye;

an object indicating device for presenting an object for a visual acuity test;

an objective refractive power inspecting device used for an objective test;

program storing means for storing therein a program for measuring completely-corrected degrees of said eyes, adjusting the completely-corrected degrees according to factors for adjusting degrees to be corrected and thereby predicting degrees to be prescribed;

input means for inputting data about the factors fop adjusting the degrees to be corrected;

program conducting means for advancing the program stored in said program storing means;

control means for activating said object indicating device and said subjective refractive power inspecting device in accordance with the program and processing the result of inspection by completely-corrected degree inspecting means and the data input by said input means thereby to predict degrees to be prescribed; and display means for displaying the prescribed degrees predicted by said control means.

7. An ophthalmic apparatus according to claim 6, wherein said control means includes storing means for storing therein quantities of correction based on degrees of near sightedness and astigmatism.

8. An ophthalmic apparatus according to claim 6, wherein said control means stores therein correction quantities varied according to the presence or absence of the history of use of a refraction correcting device and the data input by said input means shows the presence or absence of the refraction correcting device.

9. An ophthalmic apparatus according to claim 6, wherein said program has different correcting procedures each including at least one of the presence or absence of anisometropia, astigmatism and oblique astigmatism and either far sightedness or near Sightedness as an element.

10. An ophthalmic apparatus according to claim 6, further including display means for describing operational procedures of an examiner, which displays procedures necessary for respective steps pursuant to the program.

11. An ophthalmic apparatus for obtaining prescribed degrees of eyes to be examined, comprising:

program storing means for storing therein a program for measuring completely-corrected degrees of said eyes, adjusting the completely-corrected degrees according to factors for adjusting degrees to be corrected and thereby predicting degrees to be prescribed;

first input means for inputting data resulting from the refractive power inspection of said each eye by used of a refractive power measuring device;

second input means for inputting data about the factors exclusive of the result of refractive power inspection;

program conducting means for advancing the program stored in said program storing means;

control means for processing the data input by said first input means and said second input means in accordance with the program thereby to predict prescribed degrees; and display means for displaying the prescribed degrees predicted by said control means.

12. An ophthalmic apparatus according to claim 11, wherein said control means includes storing means for storing therein quantities of correction based on degrees of near sightedness and astigmatism.

13. An ophthalmic apparatus according to claim 11, wherein said control means stores therein correction quantities varied according to the presence or absence of the history of use of a refraction correcting device and the data input by said second input means shows the presence or absence of the history of use of the refraction correcting device.

14. An ophthalmic apparatus according to claim 11, wherein said program has different correcting procedures each including at least one of the presence or absence of anisometropia, astigmatism and oblique astigmatism and either far sightedness or near sightedness as an element.

15. An ophthalmic apparatus according to claim 11, further including display means for describing operational procedures of an examiner, which displays procedures necessary for respective steps pursuant to the program.

* * * * *